US008016887B1

(12) United States Patent
Castro

(10) Patent No.: US 8,016,887 B1
(45) Date of Patent: Sep. 13, 2011

(54) SPINAL IMPLANT WITH OVERLAY

(75) Inventor: Frank Castro, Louisville, KY (US)

(73) Assignee: Cardinal Spine, LLC, Louisville, KY (US)

( * ) Notice: Subject to any disclaimer, the term of this patent is extended or adjusted under 35 U.S.C. 154(b) by 288 days.

(21) Appl. No.: 12/319,674

(22) Filed: Jan. 9, 2009

Related U.S. Application Data

(63) Continuation-in-part of application No. 12/221,779, filed on Aug. 6, 2008, which is a continuation of application No. 11/089,103, filed on Mar. 24, 2005, now Pat. No. 7,435,261.

(51) Int. Cl.
*A61F 2/44* (2006.01)

(52) U.S. Cl. ................................. 623/17.11

(58) Field of Classification Search ..... 623/17.11–17.16
See application file for complete search history.

(56) References Cited

U.S. PATENT DOCUMENTS

| | | | |
|---|---|---|---|
| 5,147,402 A | 9/1992 | Bohler et al. | |
| 5,192,327 A * | 3/1993 | Brantigan | 623/17.11 |
| 5,425,772 A | 6/1995 | Brantigan | |
| 5,558,674 A | 9/1996 | Heggeness et al. | |
| 5,609,635 A | 3/1997 | Michelson | |
| 5,766,252 A | 6/1998 | Henry et al. | |
| 6,066,175 A * | 5/2000 | Henderson et al. | 623/17.11 |
| 6,090,143 A | 7/2000 | Meriwether et al. | |
| 6,117,174 A | 9/2000 | Nolan | |
| 6,159,245 A * | 12/2000 | Meriwether et al. | 623/17.11 |
| 6,231,610 B1 | 5/2001 | Geisler | |
| 6,302,914 B1 * | 10/2001 | Michelson | 623/17.16 |
| 6,395,030 B1 * | 5/2002 | Songer et al. | 623/17.11 |
| 6,409,766 B1 * | 6/2002 | Brett | 623/17.16 |
| 6,432,107 B1 | 8/2002 | Ferree | |
| 6,491,724 B1 | 12/2002 | Ferree | |
| 6,537,320 B1 | 3/2003 | Michelson | |
| 6,569,201 B2 | 5/2003 | Moumene et al. | |
| 6,660,038 B2 | 12/2003 | Bayer, II et al. | |
| 6,712,852 B1 | 3/2004 | Chung et al. | |
| 6,746,484 B1 | 6/2004 | Lin et al. | |
| 6,761,738 B1 * | 7/2004 | Boyd | 623/17.11 |
| 6,767,367 B1 | 7/2004 | Michelson | |
| 6,997,953 B2 | 2/2006 | Chung et al. | |
| 7,182,782 B2 | 2/2007 | Kirschman | |
| 2003/0125739 A1 | 7/2003 | Bagga et al. | |
| 2004/0064184 A1 | 4/2004 | Chung et al. | |
| 2004/0073314 A1 * | 4/2004 | White et al. | 623/17.15 |
| 2004/0153155 A1 | 8/2004 | Chung et al. | |
| 2004/0153160 A1 * | 8/2004 | Carrasco | 623/17.15 |
| 2005/0071006 A1 | 3/2005 | Kirschman | |
| 2005/0071008 A1 * | 3/2005 | Kirschman | 623/17.11 |
| 2006/0287725 A1 * | 12/2006 | Miller | 623/17.11 |
| 2007/0016295 A1 | 1/2007 | Boyd | |
| 2008/0021476 A1 | 1/2008 | Kirschman | |

(Continued)

OTHER PUBLICATIONS

Barack, R. L. Revision Total Hip Arthroplasty: The Femoral Component. J. Am Acad Orthop Surg 1995; 3(2); 79-85. USA.

(Continued)

*Primary Examiner* — Eduardo C Robert
*Assistant Examiner* — Mary Hoffman
(74) *Attorney, Agent, or Firm* — Kenneth F. Pearce

(57) ABSTRACT

A spinal implant and an overlay for interlocking with the face of the spinal implant. Grooves and/or channels of the overlay interlock with the face of the implant. The overlay assists in securing the implant within the surgically created cavity.

8 Claims, 20 Drawing Sheets

U.S. PATENT DOCUMENTS

2010/0004752 A1 * 1/2010 White et al. ............... 623/17.16

OTHER PUBLICATIONS

Castro, F. P., Jr. Stingers, Cervical Cord Neurapraxia, and Stenosis. Clin Sport Med 2003; 22: 483-492. USA.

Majd M.E, Vadhva, M., Holt R.T. Anterior Cervical Reconstruction Using Titanium Cages With Anterior Plating. Spine 1999; 24 (15): 1604-1610. USA.

Park J.B., Cho Y.S., Riew, K.D. Development of Adjacent-Level Ossification in Patient with an Anterior Cervical Plate. J. Bone Surg. 2005; 87-A: 558-563. USA.

* cited by examiner

FIG 9

Supplying a length of brace or implant that has a plurality of spaced apart trapezoidal platforms where each inward trapezoidal platform has posts that extend in opposite directions from the trapezoidal platform

Measuring the cavity where the implant or brace is to be inserted

Severing the brace or implant at one or more cross-sections to size the brace or implant to be inserted into the cavity

Fitting the brace or implant into the cavity such that one of the posts is generally parallel the dura mater

Packing the brace or implant with osteogenic material or substances

FIG 10

Supplying a length of brace or implant that has a plurality of spaced apart trapezoidal platforms where each inward trapezoidal platform has posts that extend in opposite directions from the trapezoidal platform

Measuring the cavity where the implant or brace is to be inserted

Severing the brace or implant at one or more cross-sections to size the brace or implant to be inserted into the cavity

Fitting the brace or implant into the cavity such that one of the posts is generally parallel the dura mater and at least one of the posts contacts the cavity wall

Packing the brace or implant with osteogenic material or substances

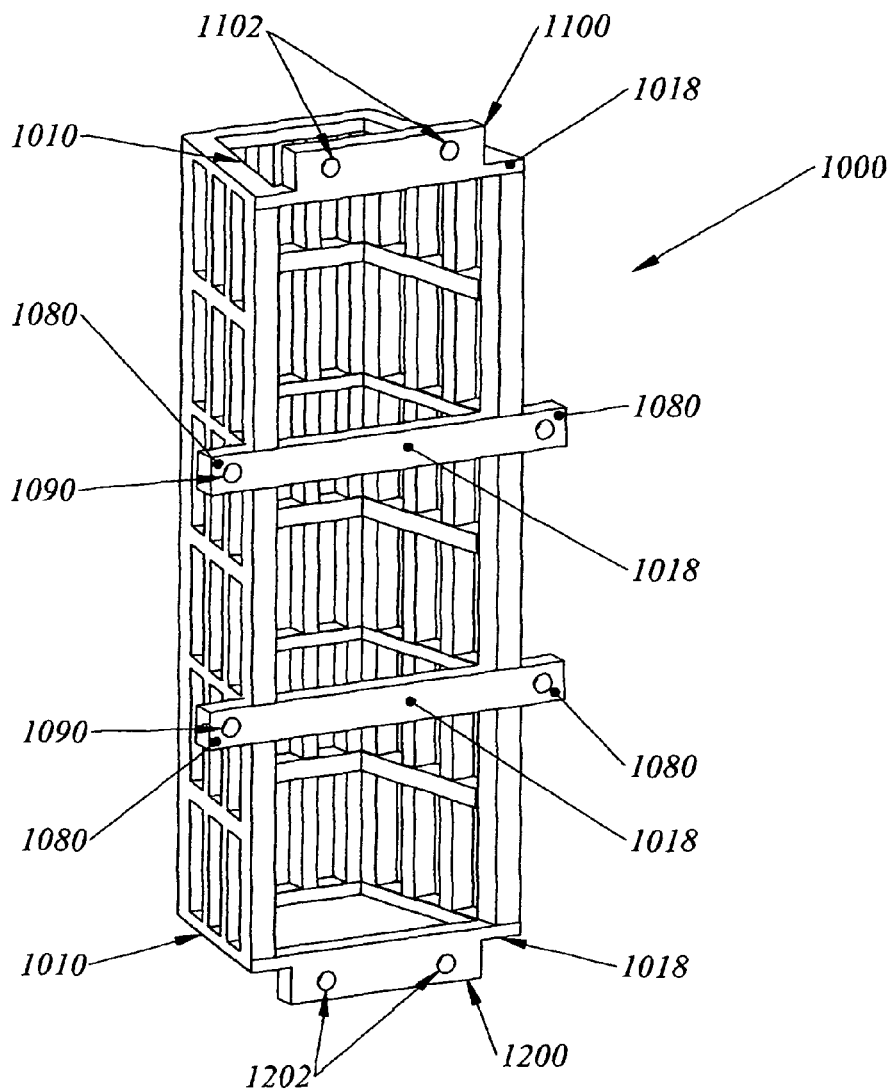
*FIG. 15*
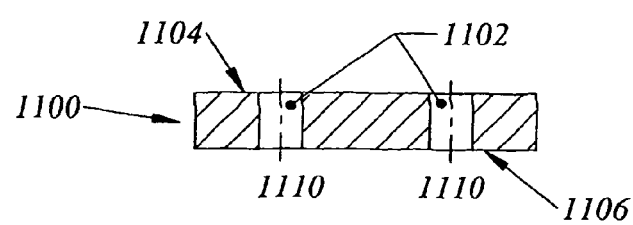
*FIG. 16*
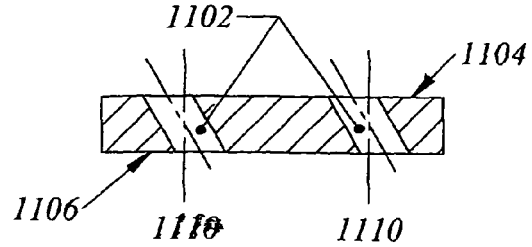

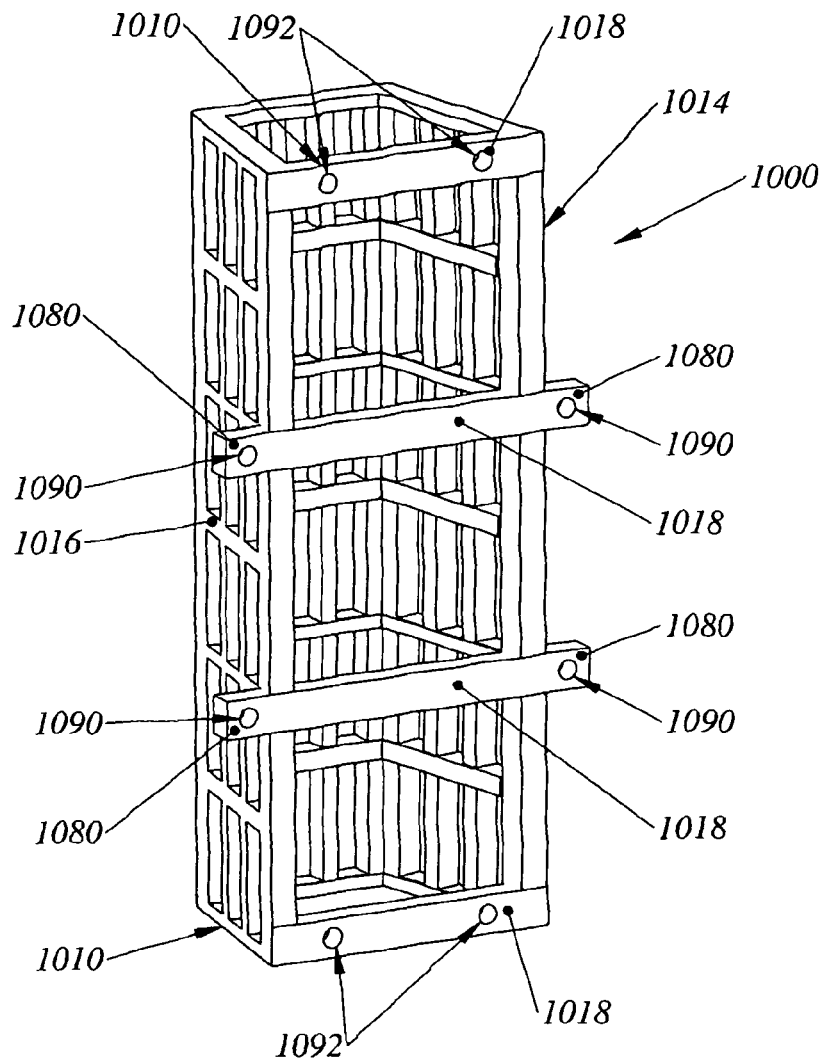
*FIG. 17*
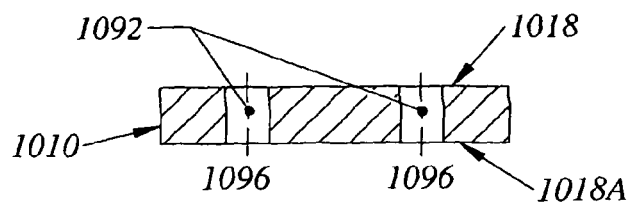
*FIG. 18*
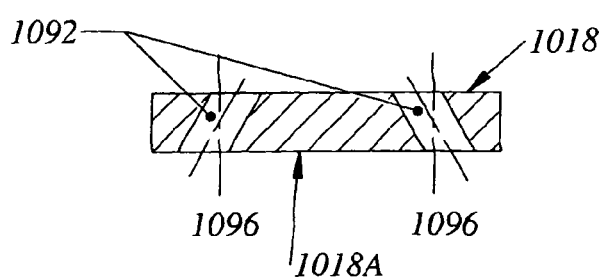

FIG 25

Improving stability for an implant capable of implantation into a surgically created cavity by supplying an implant comprising a face including a first vertical post, a second vertical post and a plurality of horizontal cross members

⬇

Providing an overlay composed of titanium, stainless steel, polymers or combinations thereof, where the overlay further comprises: a) an outward generally smooth surface; b) an indentured inward surface for interlocking with the face; c) sidewalls extending between the outward generally smooth surface and the indentured inward surface; and d) one or more apertures extending through the overlay

⬇

Aligning the indentured inward surface of the overlay with the face of the implant

⬇

Inserting fasteners through one or more of the apertures for affixing the overlay to bone

FIG 26

Improving stability for an implant capable of implantation into a surgically created cavity by supplying an implant comprising a face including a first vertical post, a second vertical post and a plurality of horizontal cross members

⬇

Providing an overlay composed of titanium, stainless steel, polymers or combinations thereof, where the overlay further comprises: a) an outward generally smooth surface; b) an indentured inward surface for interlocking with the face, wherein the indentured inward surface includes a first groove corresponding to the first vertical post, a second groove corresponding to the second vertical post and channels corresponding to the plurality of cross members; c) sidewalls extending between the outward generally smooth surface and the indentured inward surface; and d) one or more apertures extending through the overlay

⬇

Aligning the indentured inward surface of the overlay with the face of the implant

⬇

Inserting fasteners through one or more of the apertures for affixing the overlay to bone

FIG 27

```
┌─────────────────────────────────────────────────────────────────────────────┐
│ Improving stability for an implant capable of implantation into a surgically│
│ created cavity by supplying an implant comprising a face including a first  │
│ vertical post, a second vertical post and a plurality of horizontal cross   │
│ members                                                                      │
└─────────────────────────────────────────────────────────────────────────────┘
                                      ⬇
┌─────────────────────────────────────────────────────────────────────────────┐
│ Providing an overlay composed of titanium, stainless steel, polymers or     │
│ combinations thereof, where the overlay further comprises: a) an outward    │
│ generally smooth surface; b) an indentured inward surface for interlocking  │
│ with the face, wherein the indentured inward surface includes a first groove│
│ corresponding to the first vertical post, a second groove corresponding to  │
│ the second vertical post and channels corresponding to the plurality of     │
│ cross members, where at least some of the grooves and channels have at least│
│ some sides intersecting at generally right angles; c) sidewalls extending   │
│ between the outward generally smooth surface and the indentured inward      │
│ surface; and d) one or more apertures extending through the overlay         │
└─────────────────────────────────────────────────────────────────────────────┘
                                      ⬇
┌─────────────────────────────────────────────────────────────────────────────┐
│ Aligning the indentured inward surface of the overlay with the face of the  │
│ implant                                                                      │
└─────────────────────────────────────────────────────────────────────────────┘
                                      ⬇
┌─────────────────────────────────────────────────────────────────────────────┐
│ Inserting fasteners through one or more of the apertures for affixing the   │
│ overlay to bone                                                              │
└─────────────────────────────────────────────────────────────────────────────┘
```

FIG 28

```
┌─────────────────────────────────────────────────────────────────────────────┐
│ Improving stability for an implant capable of implantation into a surgically│
│ created cavity by supplying an implant comprising a face including a first  │
│ vertical post, a second vertical post and a plurality of horizontal cross   │
│ members                                                                      │
└─────────────────────────────────────────────────────────────────────────────┘
                                      ⬇
┌─────────────────────────────────────────────────────────────────────────────┐
│ Providing an overlay composed of titanium, stainless steel, polymers or     │
│ combinations thereof, where the overlay further comprises: a) an outward    │
│ generally smooth surface; b) an indentured inward surface for interlocking  │
│ with the face, wherein the indentured inward surface includes a first groove│
│ corresponding to the first vertical post, a second groove corresponding to  │
│ the second vertical post and channels corresponding to the plurality of     │
│ cross members, where at least some of the grooves and channels have at least│
│ some sides intersecting at generally right angles; c) sidewalls extending   │
│ between the outward generally smooth surface and the indentured inward      │
│ surface; and d) one or more apertures extending through the overlay         │
└─────────────────────────────────────────────────────────────────────────────┘
                                      ⬇
┌─────────────────────────────────────────────────────────────────────────────┐
│ Aligning the indentured inward surface of the overlay with the face of the  │
│ implant such that the apertures are transverse to the face of the implant   │
└─────────────────────────────────────────────────────────────────────────────┘
                                      ⬇
┌─────────────────────────────────────────────────────────────────────────────┐
│ Inserting fasteners through one or more of the apertures for affixing the   │
│ overlay to bone                                                              │
└─────────────────────────────────────────────────────────────────────────────┘
```

FIG 29

| Improving stability for an implant capable of implantation into a surgically created cavity by supplying an implant comprising a face including a first vertical post, a second vertical post and a plurality of horizontal cross members |

⇓

| Providing an overlay composed of titanium, stainless steel, polymers or combinations thereof, where the overlay further comprises: a) an outward generally smooth surface; b) an indentured inward surface for interlocking with the face, wherein the indentured inward surface includes a first groove corresponding to the first vertical post, a second groove corresponding to the second vertical post and channels corresponding to the plurality of cross members, where at least some of the grooves and channels have at least some sides intersecting at generally right angles; c) sidewalls extending between the outward generally smooth surface and the indentured inward surface; and d) one or more apertures extending through the overlay |

⇓

| Aligning the indentured inward surface of the overlay with the face of the implant such that the apertures are positioned above and below the face of the implant |

⇓

| Inserting fasteners through one or more of the apertures for affixing the overlay to bone |

SPINAL IMPLANT WITH OVERLAY

This application is a Continuation-In-Part of pending application Ser. No. 12/221,779, entitled—Spinal Method and Method of Using Spinal Implant—filed on Aug. 6, 2008 that is a continuation of Application for Letters patent Ser. No. 11/089,103, entitled—Spinal Method and Method of Using Spinal Implant—filed on Mar. 24, 2005, now U.S. Pat. No. 7,435,261 B2 issued Oct. 14, 2008.

BACKGROUND OF THE INVENTION

1. Field of the Invention

Among other things, the present invention is related to an overlay for an implant or the combination of an implant and the overlay. The overlay is indentured and can interlock with the face of the implant. One or more fasteners secure the overlay to bone and the implant.

2. Description of the Previous Art

1) US Publish Patent Application No. 2003/0125739 A1—Bagga, et al. discloses a bioactive spinal implant and method of manufacture. Among other things, it does not appear that the Bagga invention practices the use of posts, supports or ties.

2) U.S. Pat. No. 6,767,367 B1—Michelson enables a spinal fusion implant having deployable bone engaging projections. Michelson teaches that the '367 implant 300 has a rotatable member 320 that is preferably frustoconical in shape. Rotatable member 320 has bone engaging projections 332 adapted to penetrably engage the bone of the adjacent vertebral bodies. Bone engaging projections 332 are preferably configured such that in a retracted position, implant 300 may be linearly inserted into the disc space. After implant 300 is inserted into the disc space, bone engaging projections 332 are moved to a deployed position to penetrably engage the endplates of each adjacent vertebral body and prevent the expulsion of implant 300 from the disc space.

3) U.S. Pat. No. 6,537,320 B1—Michelson enables a self-broaching, rotable, push-in interbody spinal fusion implant and method for its deployment. Among other things, it does not appear that the Michelson invention practices the use of posts, supports or ties.

4) U.S. Pat. No. 5,609,635—Michelson enables a lordotic interbody spinal fusion implant. The Michelson Summary of the Invention teaches that the '635 modular implants are generally wedge-shaped that have upper and lower surfaces conforming to the contours of the vertebral endplates, which contours include but are not limited to being relatively flat or convex. Michelson states, "As the disc spaces in the lumbar spine are generally lordotic, said implants in the preferred embodiment would be taller anteriorly, that is at the implant's insertion end, and less tall posteriorly, that is at the implant's trailing end. To introduce an implant that is taller at its insertion end than the space available at the posterior aspect of the disc space, even when that disc space is optimally distracted, is problematic."

5) U.S. Pat. No. 6,302,914 B1—Michelson enables a lordotic interbody spinal fusion implant. The '914 Patent is a continuation Patent of the U.S. Pat. No. 5,609,635—Michelson Patent.

6) U.S. Pat. No. 6,066,175—Henderson, et al. enables a fusion stabilization chamber. Mesh cage 41 sits between vertebral bodies 43 and 45. Intervertebral discs 46 and 47 flank the vertebral bodies. The spinal cord is indicated by reference numeral 53. Cage 41 fills the space previously occupied by another such disc. The cage includes barrel vaults 48 and 49, and has flanges 50 and 51 which help to anchor the cage on the vertebral bodies and provide means for attachment thereto. The Henderson flanges also prevent the cage from being inadvertently tapped into the spinal cord, and they also distribute the shear and bending moment and thus increase the stability of the device. The flanges also provide one or more additional holes to accommodate more screws for affixing the device to the vertebral bodies. Both the flanges and barrel vaults are preferably integral with the cage. The barrel vaults can be either threaded or non-threaded. The screws which are inserted through the barrel vaults are preferably of the locking type, so that they lock into the barrel vaults when fully inserted. The cage is preferably rectangular when viewed from the top or the bottom. The cage may be constructed such that the bottom (the side pointed towards the spinal cord) is solid and not made of mesh. The top of the cage could also be solid. A mesh structure is most necessary on the sides of the cage, where the cage abuts the vertebral bodies, so as to promote fusion between the bone chips or bone substitute material inside the cage and the adjacent vertebral bodies.

7) U.S. Pat. No. 5,766,252—Henry, et al. enables an interbody spinal prosthetic implant and method. Among other things, the Henry device practices threaded hole 38 and longitudinal struts 84.

8) U.S. Pat. No. 5,425,772—Brantigan enables a prosthetic implant for intervertibral spinal fusion. Among other things, the '772 device practices traverse teeth or serrations 19 where the teeth have sharp peaks 19a, slopping walls 19b and valleys 19c.

9) U.S. Pat. No. 5,147,402—Bohler, et al. enables an implant for ingrowth of osseous tissue. Among other things, Bohler does not appear to practice a generally wedge shaped cage.

10) U.S. Pat. No. 6,746,484—Liu, et al. enables a spinal implant. Among other things, the Liu disclosure teaches that tool 22 has a milling cutter 23, central cutting portion 24 and two non-cutting portions 31, 36 arranged at opposite ends of central cutting portion 24. Non-cutting portions 31, 36 have height h corresponding to the intersomatic space and permitting uniform, symmetrical cutting of a predetermined length through a central region of both vertebral plates 15, 16. The geometry of portions 24, 31, 36 is determined for preparing the intersomatic space with the geometry of implant 1 to restore the natural lordosis of the intervertebral space, and correspondingly the distances represented by h and d1 are approximately equal.

11) U.S. Pat. No. 6,231,610 B1—Geisler enables an anterior cervical column support device. The '610 apparatus utilizes serrations on the load bearing surfaces and two screw holes.

12) U.S. Pat. No. 6,660,038 B2—Boyer, et al. enables skeletal reconstruction cages. The Boyer Patent discloses an end cap 210 suitable for coupling to central shaft 160 includes an outer wall 212, as well as a central hole disposed along axis 213 with a lower inner wall 214, an upper inner wall 216, and an inner ridge portion 218. Lower inner wall 214 extends about a depth $H_2$ and is sized to fit snugly on an upper or lower portion 182, 184 of central shaft 160 with an upper or lower face 162, 164 abutting a shoulder 218. Preferably, upper inner wall 216 has a dimension that is about the same as dimension $D_5$ of hole 178 of central shaft 160. End cap 210 is symmetrical about line 220, and is generally oblong in shape with first and second widths $W_2$, $W_3$. Notably, while outer wall 176 of central shaft 160 is generally circular, outer wall 212 of end cap 210 is generally oblong, so that a generally I-shaped skeletal reconstruction cage may be formed when a pair of end caps 210 are placed on central shaft 160.

13) U.S. Pat. No. 6,491,724—Ferree enables a spinal fusion cage with lordosis correction. Among other things, the '724 Patent teaches, "In the preferred embodiment, the anterior portion 112 includes mating members 120 and 122 with teeth 124 or other features to form a locking or ratchet mechanism, as shown. Whatever apparatus is used, the purpose is to maintain the height of the anterior portion of the cage at a desired level consistent with lordosis upon installation."

14) U.S. Pat. No. 6,117,174—Nolan enables a spinal implant device. Among other things, the '174 apparatus utilizes disc 14 made of the same material as body 12. Inner surfaces of legs 18 and 20 are curved.

15) US Published Patent Application No. 20070016295—Boyd discloses a reinforced molded implant formed of cortical bone. Boyd reads, "Implant 10 defines a longitudinal axis 11 and includes a first strut 12, a second strut 14 spaced from first strut 12, and cross-member 16 extending therebetween. First strut 12 and second strut 14 are each positioned to lie in a plane substantially parallel to longitudinal axis 11. Implant 10 includes at least one additional cross-member 16 A connecting first strut 12 and second strut 14. It is understood that in alternative embodiments implant 10 can have one or a plurality of cross-members connecting first strut 12 to second strut 14."

16) U.S. Pat. No. 6,090,143—Meriwether, et al. enables a box cage for intervertebral body fusion. Meriwether reads, "FIG. 6 illustrates a further embodiment of the invention which is a slight modification of that shown in FIG. 4. In the embodiment of FIG. 6, rather than having a rectangular longitudinal cross-section, it is trapezoidal such that the resulting cage member, indicated generally by numeral 110, is wedge-shaped. The assembled cage comprises a box-like base 112 and a cover 114 dimensioned to fit over the base much like the cover on a shirt box. The height dimension of the rightmost ends of the base and cover are greater than the height dimension of the corresponding, opposed left side ends, thus providing the desired wedge shape. Upwardly projecting ribs 116 and 118 extend along the rear and front side edges, respectfully, and likewise, the base 112 includes longitudinally extending ribs 120 and 122 projecting downwardly from the undersurface of the base along the side edges thereof. The right and left ends of the base 112 and the cover 114 include semi-circular cut-outs as at 124 and 126 and 128-130 such that when the cover 114 is placed upon the base 112, circular apertures are formed. These apertures are adapted to receive a tapered screw 132 therein. The slope of the taper of the screw is designed to correspond to that of the cage assembly 110 such that when the screw 132 is threaded into the circular opening defined by arcuate cut-outs 124 and 126 and advanced by turning until the leading end 134 of the screw enters the circular aperture 128-130, further turning of the screw will raise the case cover 114 relative to its base 112, allowing adjustment of the cage height following positioning thereof between adjacent vertebral bodies."

17) U.S. Pat. No. 6,159,245—Meriwether, et al. enables a box cage for intervertebral body fusion. The '143 Meriwether Patent is a continuation of U.S. Pat. No. 6,090,143-Meriwether, et al.

18) U.S. Pat. No. 6,432,107—Ferree enables enhanced surface area spinal fusion devices. The '107 Patent teaches, "The device 200 fits into slots 204 and 206 made in upper and lower vertebrae 208 and 210, respectively, allowing the lower section to fuse within the body of the lower vertebrae 210, and the upper section to fuse within the body of the upper vertebrae 208. Thus, in contrast to existing devices, the device 200 and the alternative embodiments disclosed herein feature considerably more intimate contact with cancellous bone due to the fact that the device is inserted directly into the cavities 204 and 206. Rather than a relatively minor amount of scraping of the end plates of the vertebrae to be distracted, the entire end portions of the device 200 which penetrate the upper and lower vertebrae make contact with cancellous bone, thereby enhancing fusion considerably. FIG. 2B is a cross-section of a vertebrae of FIG. 2A as viewed from a top-down perspective, showing how the device fits tightly along the entire walls of the channels created in the vertebrae." Among other things, the Ferree device does not allow the surgeon to see through the device after insertion into the surgical cavity.

19) U.S. Pat. No. 6,569,201—Moumene, et al. enables a hybrid composite interbody fusion device. The '201 Patent reads, " . . . there is provided a non-resorbable support 1 having an upper contact surface 3, and a lower contact surface 5, these surfaces being connected by side surfaces 7, 9, each side surface forming a portion of the outer surface 11. Osteoconductive pore 2 passes completely through the support 1 from lower surface 5 to upper contact surface 3, and opens onto upper and lower openings 15, 17 formed in the upper 3 and lower 5 contact surfaces. Osteoconductive pore 2 forms a void 23 within the support and defines an inner surface 13, and opens onto side surface openings 19, 21 formed in side surfaces 7, 9. Void section 23 is suitable for housing a bone growth material such as bone chips (not shown). In this case, the non-resorbable support 1 has a cage shape." Among other things, Moumene does not teach a span of receptacles.

SUMMARY OF THE INVENTION

Unlike traditional spinal implants, the present invention provides a spinal implant that can be packed with bone graft and/or other osteogenic materials or substances after the spinal implant has been inserted into a surgically created cavity of one or more vertebra. Prior to packing the receptacle with osteogenic substances, the surgical team can view the dura mater of the spinal cord. When inserting the brace, during a surgical procedure, the wedge-like shape of the implant assists the surgical team in not impinging the spinal cord with the brace. Post operative and prior to complete arthrodesis, the generally wedge-like shape of the implant inhibits extrusion of the brace against the spinal cord.

Another feature of the present invention is an overlay for an implant. The overlay can interlock with the face of an implant implanted into a surgically created cavity. One or more apertures about one or more margins of the overly receive fasteners, such as screws, secure the overlay to bone. The outward surface of the overlay is generally smooth and the inward surface is indentured for interlocking with the face of the implant.

An aspect of the present invention is to provide a generally wedge-shaped spinal surgical implant or brace.

Still another aspect of the present invention is to provide a spinal implant having a trapezoidal shaped platform or divider.

It is another aspect of the present invention to enable a method of implanting the generally trapezoidal shaped brace into a surgically created cavity of one or more vertebra.

Yet another aspect of the present invention is to provide a receptacle of an implant that after insertion into the surgically created cavity allows the surgical team to view the dura mater of the spinal cord through an opening of the receptacle.

Still another aspect of the present invention is to provide a receptacle of an implant that allows the packing of bone graft and/or osteogenic materials or substances through an opening facing the surgical team after the receptacle is inserted into the surgically created cavity.

It is still another aspect of the present invention to provide an implant having select embodiments that can be implanted through the patient's frontal or rearward side.

Yet still another aspect of the present invention is to provide a brace that includes a span of conjoined receptacles.

It is still another aspect of the present invention to provide an implant that includes a span of consecutively joined receptacles, where the span can be severed across a first cross-section or a first cross-section and a second cross-section to create a custom fitted implant for the surgically created cavity.

Still another aspect of the present invention is to provide an implant having a plurality of apertures.

It is another aspect of the present invention to provide an implant that includes one or brakes having bores for receiving fasteners such as bone screws.

Yet another aspect of the present invention is to provide an implant that includes upper and lower plates having one or more bores for receiving fasteners.

Still another aspect of the present invention is to provide an overlay capable of interlocking with an implant.

It is still another aspect of the present invention to provide an indentured overlay for interlocking with a face of an implant.

Yet still another aspect of the present invention is to provide an indentured overlay that includes a plurality of grooves and/or channels.

An embodiment of the present invention can be described as an implant capable of implantation into a surgically created cavity between a superior vertebra and an inferior vertebra and an overlay capable of covering the implant: I) the implant, comprising: a) a series of dividers; b) a first corner post contacting first inward corners of the series; c) a second corner post contacting second inward corners of the series; d) a third corner post contacting first outward corners of the series; and e) a fourth corner post contacting second outward corners of the series; and II) the overlay, capable of covering the implant, comprising: a) an outward generally smooth surface; b) an inward surface opposite the outward generally smooth surface, wherein the inward surface comprises indentations for interlocking with outward edges of the series, the third corner post and the fourth corner post; c) sidewalls extending between the outward generally smooth surface and the inward surface; and d) one or more apertures extending through the overlay, wherein the one or more apertures are proximate to one or more margins of the overlay.

Another embodiment of the present invention can be described as an overlay for interlocking with a face of an implant capable of generally vertical implantation into a surgically created cavity between a superior vertebra and an inferior vertebra, wherein the face comprises a first vertical member, a second vertical member and a plurality of cross members interconnected with the first vertical member and the second vertical member; the overlay comprising: a) a quadrilateral outward generally smooth surface; b) a quadrilateral inward surface opposite said outward generally smooth surface, wherein the quadrilateral inner surface comprises indentations for interlocking with the face of the implant; c) sidewalls extending between the quadrilateral outward generally smooth surface and the quadrilateral inward surface; and d) one or more apertures extending through said overlay, wherein said one or more apertures are proximate to one or more margins of the overlay.

Another embodiment of the current invention can be described as a method of improving stability of an implant capable of implantation into a surgically created cavity between a superior vertebra and an inferior vertebra, wherein the implant comprises a face including a first vertical post, a second vertical post and a plurality of horizontal cross members interconnected with the first vertical post and the second vertical post; said method comprising the steps of: a) providing an overlay composed of titanium, stainless steel, polymers or combinations thereof, wherein said overlay further comprises: i) an outward generally smooth surface; ii) an indentured inward surface opposite the outward generally smooth surface for interlocking with the face; iii) sidewalls extending between the outward generally smooth surface and the indentured inward surface; and iv) one or more apertures extending through the overlay, wherein the one or more apertures are proximate to one or more margins of the overlay; b) aligning the indentured inward surface of the overlay with the face of the implant; and c) inserting fasteners through one or more of the apertures for affixing the overlay to bone.

Another embodiment of the present invention can be described as an overlay for an implant capable of generally vertical implantation into a surgically created cavity between a superior vertebra and an inferior vertebra; said overlay comprising: a) an outward generally smooth surface; b) an indentured inward surface opposite the outward generally smooth surface, wherein the indentured inner surface comprises: i) a first vertical groove; ii) a second vertical groove; and iii) a plurality of transverse channels connected with the first vertical groove and the second vertical groove; c) sidewalls extending between the outward generally smooth surface and the indentured inner surface; and d) one or more apertures extending through the overlay, wherein one or more apertures are proximate to one or more margins of the overlay.

It is the novel and unique interaction of these simple elements which creates the apparatus and methods, within the ambit of the present invention. Pursuant to Title 35 of the United States Code, descriptions of preferred embodiments follow. However, it is to be understood that the best mode descriptions do not limit the scope of the present invention.

BRIEF DESCRIPTION OF THE DRAWINGS

FIG. 9 is an exemplification of the steps of an embodiment of the current method.

FIG. 10 is a diagrammatic representation of the steps of another embodiment of the present invention.

FIG. 15 is a frontal perspective of another embodiment of implant of the present invention.

FIG. 16 is a cross section of an embodiment of a plate of the present invention.

FIG. 17 is a frontal perspective of yet another embodiment of implant of the present invention.

FIG. 18 is a cross section of an embodiment of an outward side and inward edge of a superior or inferior divider of the present invention.

FIG. 25 is an exemplification of the steps of an embodiment of the current method of improving stability of an implant.

FIG. 26 is a diagrammatic representation of the steps of another embodiment of the present invention of improving stability of an implant.

FIG. 27 is another diagrammatic representation of the steps of still another embodiment of the present invention of improving stability of an implant.

FIG. 28 is yet another exemplification of the steps of yet another embodiment of the present invention of improving stability of an implant.

FIG. 29 is another diagrammatic representation of the steps of an embodiment of the current method of improving stability of an implant.

DESCRIPTION OF THE PREFERRED EMBODIMENTS

Figure 1:
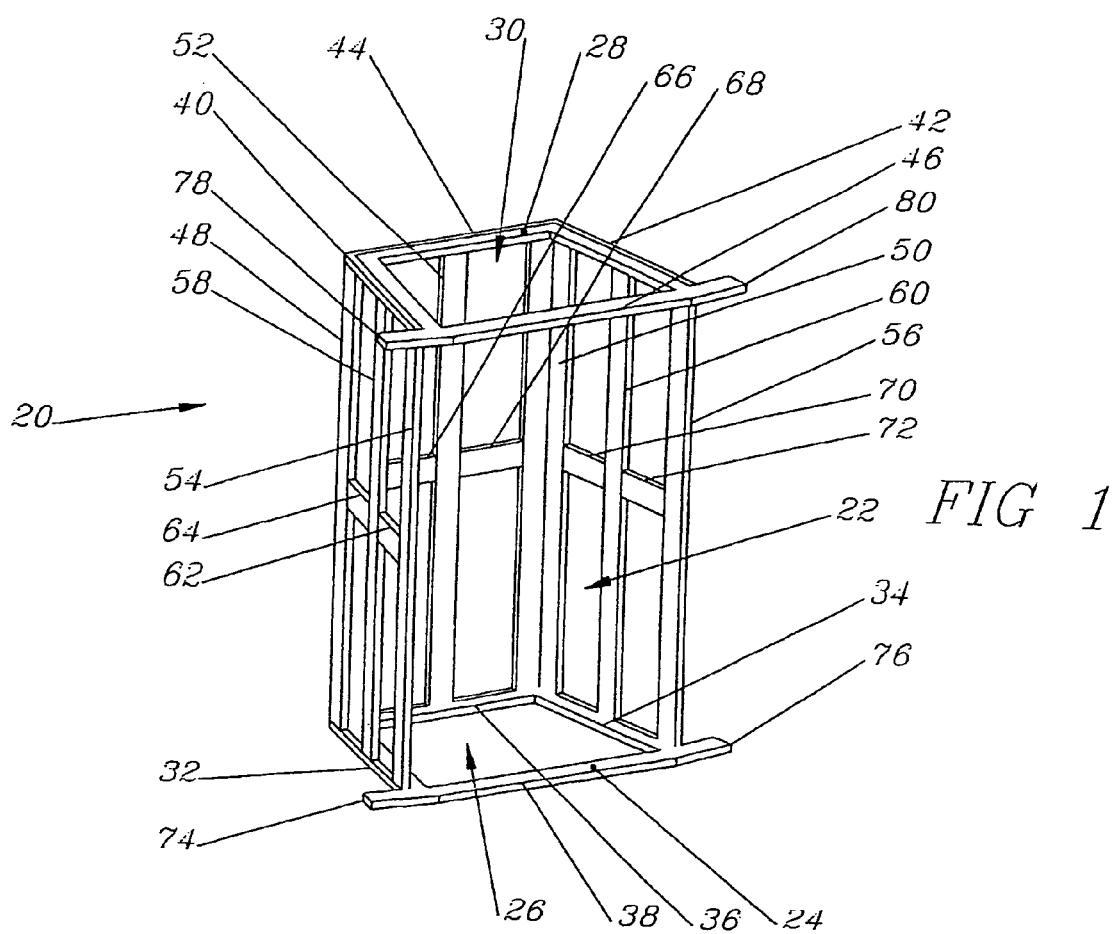
FIG. 1 is a frontal perspective of an embodiment of a receptacle of the present invention.

Although the disclosure hereof is detailed to enable those skilled in the art to practice the invention, the embodiments published herein merely exemplify the present invention.

In the most general sense, the present invention is a brace or implant that can be inserted into a cavity of the spinal column. Surgical removal of at least a part of one or more vertebra creates the cavity that will receive the implant. It has been discovered that many embodiments of the current implant can be useful for cervical spine surgeries and can assist in stabilization of the postoperative spine. And many of the preferred embodiments of the present invention are particularly suited for corpectomy or partial corpectomy procedures.

After insertion of the brace into the cavity, the brace assists in stabilizing the spinal column against rotational movement and also resists the compression forces associated with gravitational forces on the spinal column. Select embodiments of the present invention can be implanted through the patient's frontal side, e.g., the frontal side of the patient's neck. Depending on the required surgical parameters, such as the length of the cavity and the number of vertebra involved in the procedure, the brace or implant can include a span of receptacles for receiving bone graft and/or other osteogenic substances. When a conjoined receptacle embodiment is practiced, the implant can be custom fitted to the desired size for the cavity into which the implant will be inserted. In one embodiment, the custom fitted implant can be created by severing through a cross-section of the brace, thereby creating two sections of the implant, including the one that is to be inserted into the cavity. In other embodiments, the custom fitted implant can be created by severing through a first cross-section and a second cross-section of the brace.

Preferred embodiments of the current spinal implant are generally trapezoidal in shape and are manufactured of titanium alloys, stainless steel, resorbable polymers or any other composition acceptable in the art. Within the scope of the present invention, it has advantageously been discovered that receptacles can have a height of approximately twelve millimeters, a width of from about six to about fifteen millimeters as measured along the narrowest parallel of the trapezoid and a depth of from about eight millimeters to about fifteen millimeters as measured along a converging side of the trapezoid. The size of implant to be inserted in the cavity is dependent upon the volume of the cavity. Prior to the surgical procedure, spans of braces of differing sizes can be provided to the surgical team—allowing the surgical team to select the appropriate volume and length for the implant to be inserted into the surgically created cavity. After a brace or implant has been inserted into the cavity, openings of the receptacles into which bone graft, osteogenic and/or arthrodesis accelerating substances are packed can have areas from about 36 millimeters$^2$ to 225 millimeters$^2$ or greater.

Each receptacle of the present invention can be provided with corner posts or supports and other posts or supports that extend the height of the receptacle. Posts and corner posts are spaced about the outer border of the receptacle. One or more ties can extend crosswise between the posts and corner posts. Corner supports and the other supports are from about one millimeter to about two millimeters wide and are situated along the outer periphery of the receptacle in such a way as to create apertures between the posts and corner posts. Depending on the volume of the implant, the apertures between the corner posts and the other posts are from about one millimeter to about two millimeters wide.

Meeting a long felt but unfilled need in the spinal surgical arts, the unique structures of the present invention allow the surgical team to view the dura mater, before a receptacle is packed with bone graft, osteogenic and/or arthrodesis accelerating substances. Allowing the surgical team to view the dura mater while inserting the implant into the cavity reduces the possibility of having the brace inadvertently contact or injure the spinal cord. At the same time, the generally trapezoidally-shaped brace also assists the surgical team in not inserting the implant against the spinal cord. The contact between the cavity wall and the wedge-like brace can inhibit the implant from contacting the spinal cord. It appears that having the apertures of select embodiments in such close proximity with the cavity's walls increases the probability of the osteogenic materials procuring a blood supply. And it is believed that increasing the blood supply to the osteogenic materials held by a receptacle enhances local areas of arthrodesis between the vertebra and the bone graft. Select preferred embodiments of the present invention are also provided with brakes to further impede the implant from contacting the spinal column.

FIG. 1 is a frontal perspective of an embodiment of a receptacle of the present invention. When implanted into a surgically created cavity of the spinal column, opening (22) of receptacle or brace (20) will face the surgical team. A first trapezoidal platform (24) includes aperture (26) and a second trapezoidal platform (28) includes aperture (30). First platform (24) includes first converging side (32), second converging side (34), shorter side (36) and longer side (38). Second platform (28) is provided with first converging side (40), second converging side (42), shorter side (44) and longer side (46). Platform (24) is spaced apart from platform (28), and corner posts (48) and (50) extend between first platform (24) and second platform (28). Intermediate of first corner post (48) and second corner post (50) is frontal post (52). Proximate longer side (38) of platform (24) and longer side (46) of platform (28) and extending between platform (24) and platform (28) are posts (54) and (56).

Although not required to practice the present invention, as shown in FIG. 1, in select preferred embodiments, positioned between corner post or support (48) and post or support (54) is post or support (58) that extends between first converging side (32) of platform (24) and first converging side of (40) of platform (28). In a similar manner, post or support (60) is positioned between corner post or support (50) and post or support (56) and extends between second converging side (34) of platform (24) and second converging side of (42) of platform (28). Select preferred embodiments can include one or more ties extending between or connecting the posts or supports.

By way of illustration, as shown in FIG. 1, tie (62) connects post (54) and post (58), tie (64) connects post (58) and post (48), tie (66) connects post (48) and post (52), tie (68) connects post (52) and post (50), tie (70) connects post (50) and post (60) and tie (72) connects post (60) and post (56). When surgical parameters mandate, one or more ties can be eliminated from brace (20). In an alternate preferred embodiment, a first tie can connect all posts positioned along the first converging side (32, 40) of implant (20), a second tie can connect all posts located near the frontal plane of brace (20) and a third tie can connect all posts positioned along the second converging side (34, 42) of receptacle (20).

When surgical parameters dictate, more than three or less than three posts can be positioned along either the first converging side, the second converging side or both of implant (20). In an alternate preferred embodiment, frontal post (52) can be eliminated. And in select preferred embodiments, instead of a plurality of ties interconnecting with the various posts, a single tie can interconnect posts (48), (50), (52), (54), (56), (58) and (60).

With reference still to FIG. 1, brake (74) extends laterally of first converging side of platform (24) and brake (76) extends laterally of second converging side of platform (24). Brake (78) extends laterally of first converging side of platform (28) and brake (80) extends laterally of second converging side of platform (28). Depending upon preselected parameters, for an embodiment employing brakes, a receptacle can be provided with one or more brakes.

Figure 2:
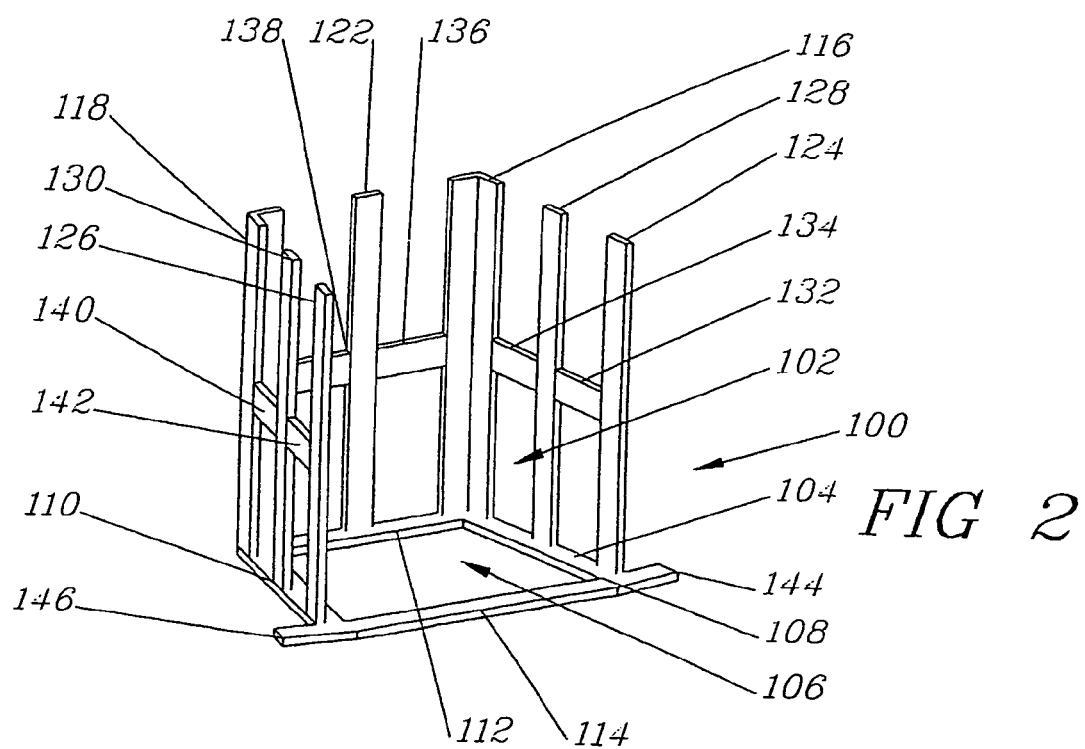
FIG. 2 is a frontal perspective of another embodiment of a receptacle of the present invention.

FIG. 2 is a frontal perspective of another embodiment of a receptacle of the present invention. When implanted into a surgically created cavity of the spinal column, opening (102) of receptacle or brace (100) will face the surgical team. Trapezoidal platform (104) includes aperture (106), first converging side (108), second converging side (110), shorter side (112) and longer side (114). First corner spike (116) and second corner spike (118) extend from shorter side (112) of platform (104). Seventh spike (122) is intermediate first corner spike (116) and second corner spike (118). Third spike (124) and fifth spike (128) extend from first converging side (108). Fourth spike (126) and sixth spike (130) extend from second converging side (110) of platform (104). As shown in FIG. 2, seven spikes are strategically extended from platform (104). However, when surgical parameters mandate, more or less than seven spikes can be extended from platform (104).

Select preferred embodiments can include one or more ties extending between or connecting the spikes. By way of illustration, as shown in FIG. 2, tie (132) connects spike (124) and spike (128), tie (134) connects spike (128) and spike (116), tie (136) connects spike (116) and spike (122), tie (138) connects spike (122) and spike (118), tie (140) connects spike (118) and spike (130) and tie (142) connects spike (130) and spike (126). When surgical parameters mandate, one or more ties can be eliminated from brace (100). In an alternate preferred embodiment, a first tie can connect all spikes positioned along the first converging side (108) of implant (100), a second tie can connect all spikes extending from shorter side (112) of brace (100) and a third tie can connect all spikes positioned along the second converging side (110) of receptacle (100). In select preferred embodiments, instead of a plurality of ties interconnecting with the various spikes, a single tie can interconnect spikes (116), (118), (122), (124), (126), (128) and (130). Brake (144) extends laterally of first converging side (108) of platform (104) and brake (146) extends laterally of second converging side (110) of platform (104).

Figure 3:
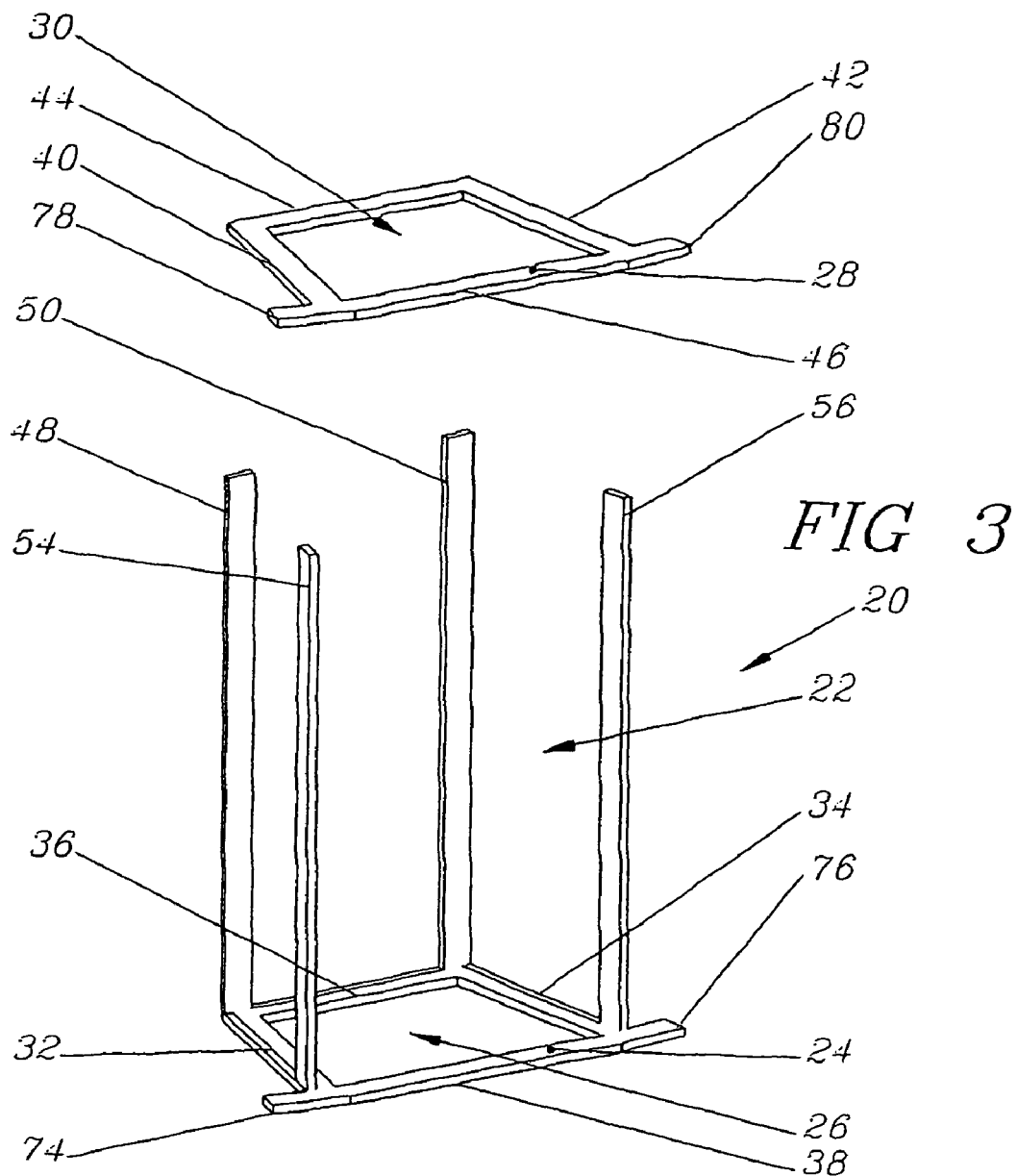
FIG. 3 is an exploded view of another embodiment of the present invention that does not utilize ties.

FIG. 3 is an exploded view of another embodiment of the present invention. When implanted into a surgically created cavity of the spinal column, opening (22) of receptacle or brace (20) will face the surgical team. A first trapezoidal platform (24) includes aperture (26) and a second trapezoidal platform (28) includes aperture (30). First platform (24) includes first converging side (32), second converging side (34), shorter side (36) and longer side (38). Second platform (28) is provided with first converging side (40), second converging side (42), shorter side (44) and longer side (46). When connected to receptacle (20), platform (28) is spaced apart from platform (24). Corner supports or posts (48) and (50) extend from first platform (24). Positioned proximate longer side (38) and extending from platform (24) are support (54) and support (56). Although not shown in FIG. 3, select preferred embodiments can include one or more ties extending between or connecting the supports. Brakes (74), (76), (78) and (80) extend laterally from the converging sides of platforms (24) and (28).

Figure 4:
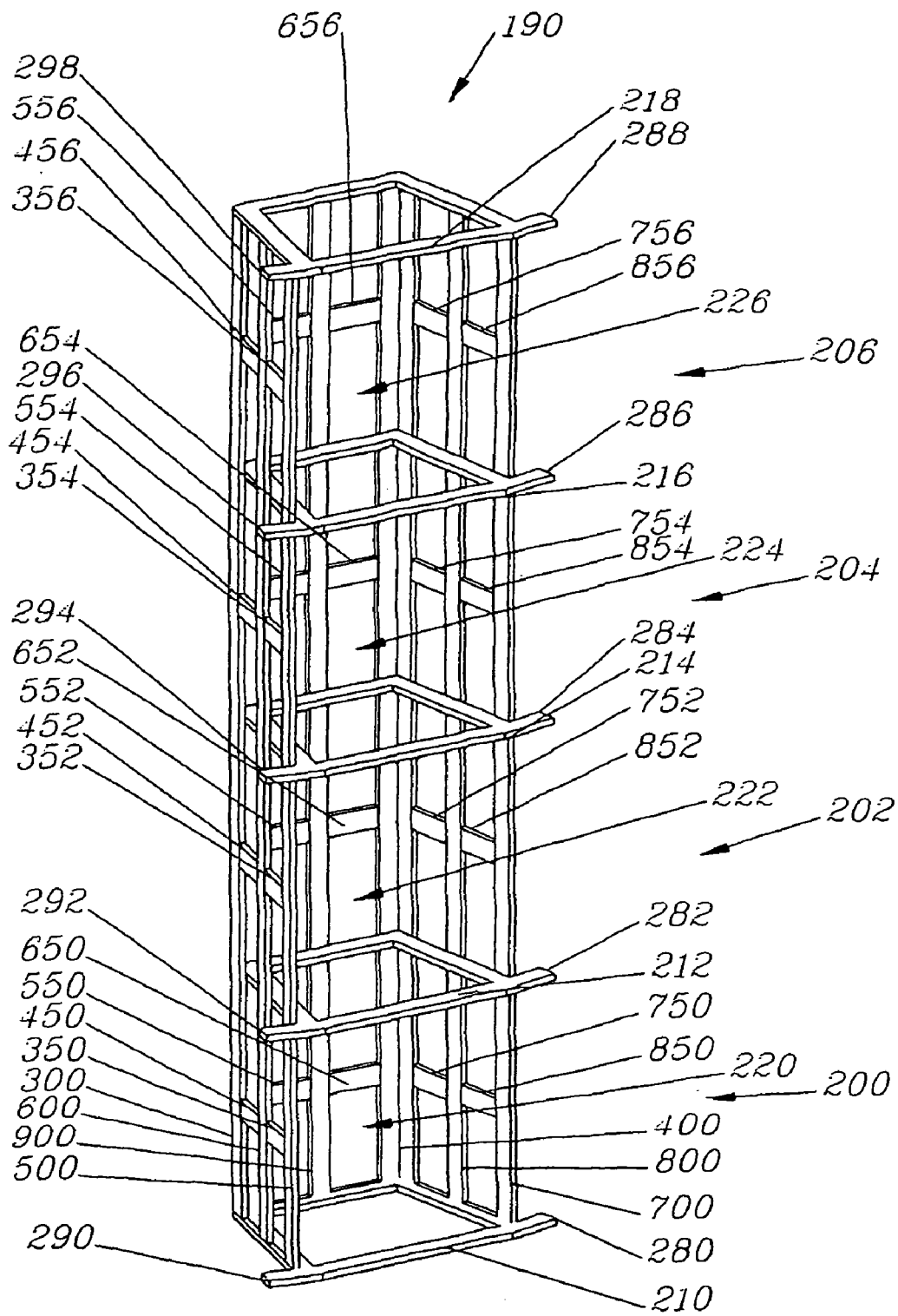
FIG. 4 is a frontal view of a span of consecutively joined receptacles.

FIG. 4 is a frontal view of span (190) of consecutively joined receptacles. As shown, by way of illustration rather than limitation, as to the number of receptacles, supports, ties or brakes, span (190) includes receptacles (200), (202), (204) and (206). Receptacle (200) includes dividers (210) and (212); receptacle (202) includes dividers (212) and (214); receptacle (204) includes dividers (214) and (216); and receptacle (206) includes dividers (216) and (218). Each divider (210, 212, 214, 216, 218) is provided with a shorter side, a longer side, a first converging side and a second converging side. Receptacles (200, 202, 204 and 206) have openings (220, 222, 224 and 226), respectively. The openings allow the surgical team to view the dura mater before one or more receptacles is packed with osteogenic substances or materials.

Receptacles (200) and (206) are end receptacles of span (190). Receptacles (202) and (204) are conjoined receptacles of span (190). Corner support (300) extends between divider (210) and divider (218) and corner support (400) extends between divider (210) and divider (218). First converging side of span (190) includes first support (500) and second support (600) extending between divider (210) and divider (218) second converging side of span (190) includes third support (700) and fourth support (800) extending between divider (210) and divider (218). Intermediate support (900) extends between divider (210) and divider (218).

With reference to receptacle (200), tie (350) connects first support (500) and second support (600); tie (450) connects second support (600) and corner support (300); tie (550) connects corner support (300) and intermediate support (900); tie (650) connects intermediate support (900) and corner support (400); tie (750) connects corner support (400) and fourth support (800); and tie (850) connects fourth support (800) and third support (700). With reference to receptacle (202), tie (352) connects first support (500) and second support (600); tie (452) connects second support (600) and corner support (300); tie (552) connects corner support (300) and intermediate support (900); tie (652) connects intermediate support (900) and corner support (400); tie (752) connects corner support (400) and fourth support (800); and tie (852) connects fourth support (800) and third support (700). With reference to receptacle (204), tie (354) connects first support (500) and second support (600); tie (454) connects second support (600) and corner support (300); tie (554) connects corner support (300) and intermediate support (900); tie (654) connects intermediate support (900) and corner support (400); tie (754) connects corner support (400) and fourth support (800); and tie (854) connects fourth support (800) and third support (700). With reference to receptacle (206), tie (356) connects first support (500) and second support (600); tie (456) connects second support (600) and corner support (300); tie (556) connects corner support (300) and intermediate support (900); tie (656) connects intermediate support (900) and corner support (400); tie (756) connects corner support (400) and fourth support (800); and tie (856) connects fourth support (800) and third support (700).

Divider (210) is provided with brakes (280) and (290); divider (212) is provided with brakes (282) and (292); divider (214) is provided with brakes (284) and (294); divider (216) is provided with brakes (286) and (296); and divider (218) is provided with brakes (288) and (298). As shown in the FIG. 4 embodiment, dividers (210 and 218) adjoin supports (300, 400, 500, 600, 700, 800 and 900), whereas dividers (212, 214 and 216) are positioned inwardly from supports (300, 400, 500, 600, 700, 800 and 900). However, depending on engineering parameters, other embodiments can include spans where each divider is flush with the supports, spans where each divider is positioned inwardly from the supports or spans where the supports are positioned inwardly from the dividers.

Figure 5:
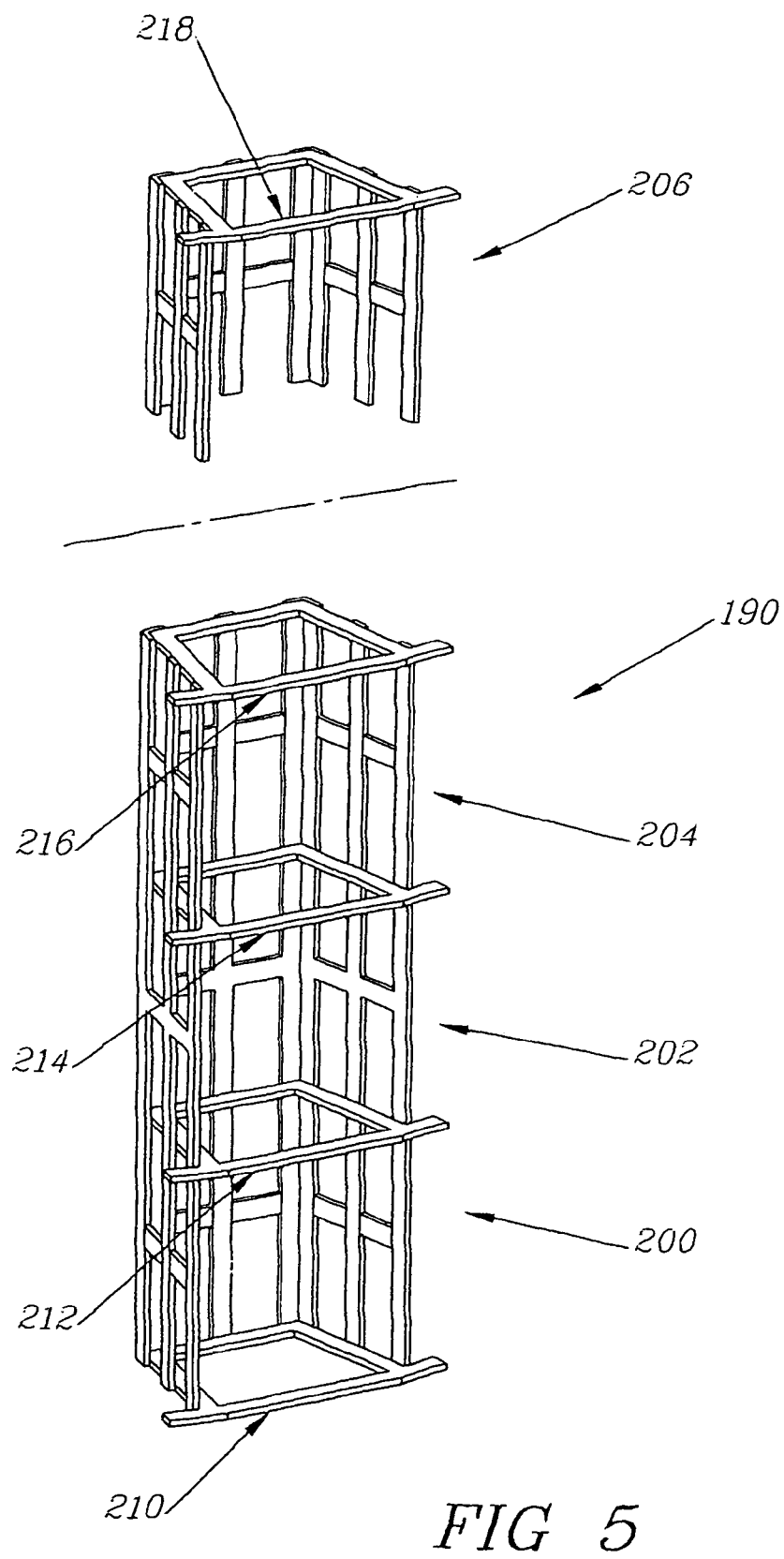
FIG. 5 is an exploded view of the invention of FIG. 4 where span (190) has been severed along a first cross-section to separate receptacle (206) away from span (190)—leaving an implant with a generally trapezoidal shaped platform or divider (210) at a first end of the implant and a generally trapezoidal shaped platform or divider (216) at a second end of the implant.

FIG. 5 is an exploded view of span (190) that has been severed along a first cross-section to separate receptacle (206) away from the remainder of span (190) and receptacles (200, 202 and 204)—leaving an implant with a generally trapezoidal shaped platform or divider (210) at a first end of the implant and a generally trapezoidal shaped platform or divider (216) at a second end of the implant. As shown in FIG. 5, each divider is positioned inwardly of the supports.

Figure 6:
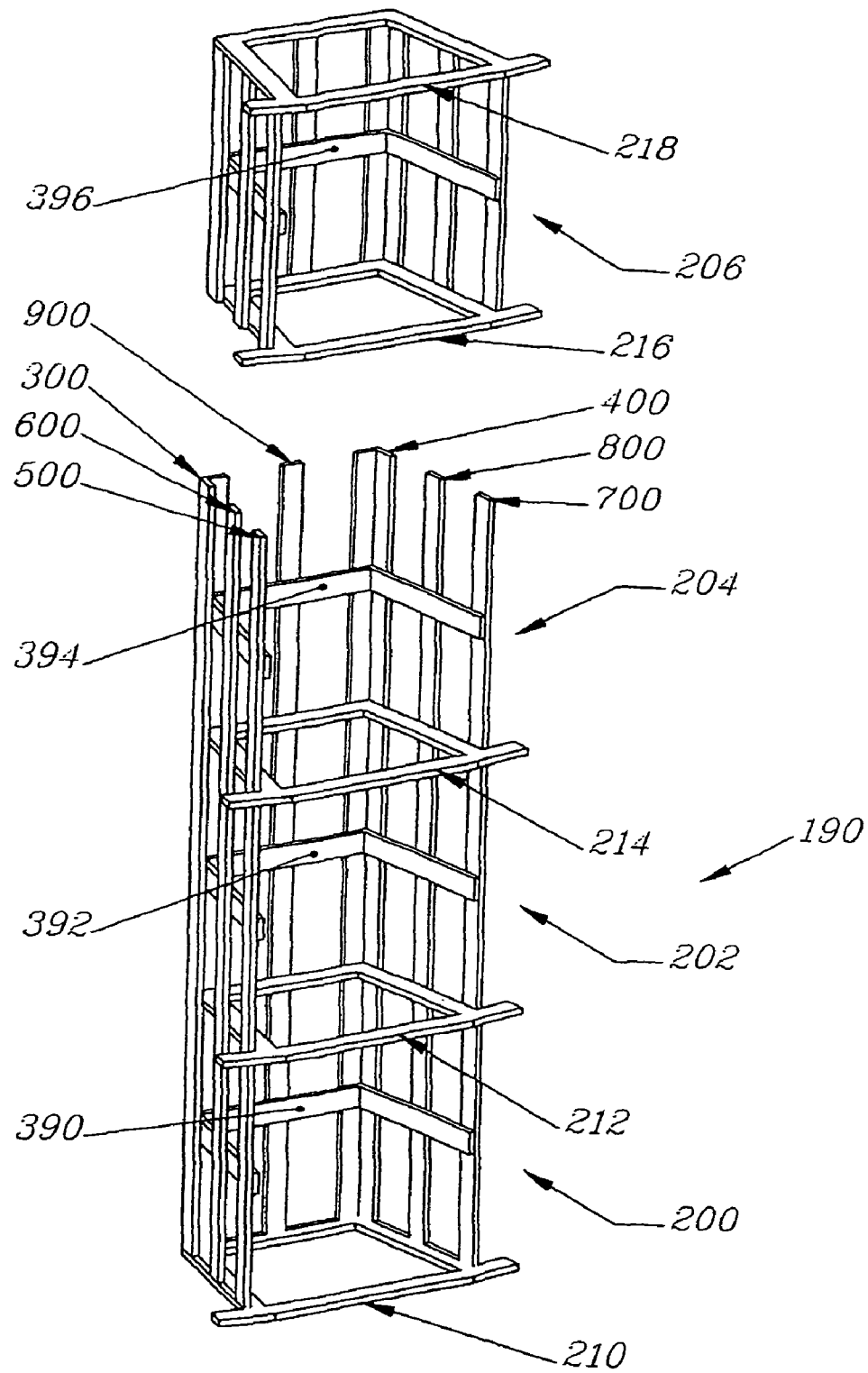
FIG. 6 is an exploded view of the invention of FIG. 4 where span (190) has been severed along a first cross-section to create an implant with a generally trapezoidal shaped divider (210) at a first end of the implant and supports or spikes (304, 404, 504, 604, 704, 804 and 904) exposed at the opposite and second end of span (190).

FIG. 6 is an exploded view of an embodiment similar to the invention of FIG. 4. Rather than a plurality of ties for receptacles (200), (202), (204) and (206), a single tie is incorporated into each receptacle. Tie (390) reinforces receptacle (200); tie (392) reinforces receptacle (202); tie (394) reinforces receptacle (204) and tie (396) reinforces receptacle (206). As shown in FIG. 6, span (190) has been severed along a first cross-section to create an implant with a generally trapezoidal shaped divider (210) at a first end of the implant and supports or spikes (300, 400, 500, 600, 700, 800 and 900) exposed at the opposite and second end of span (190).

Figure 7:
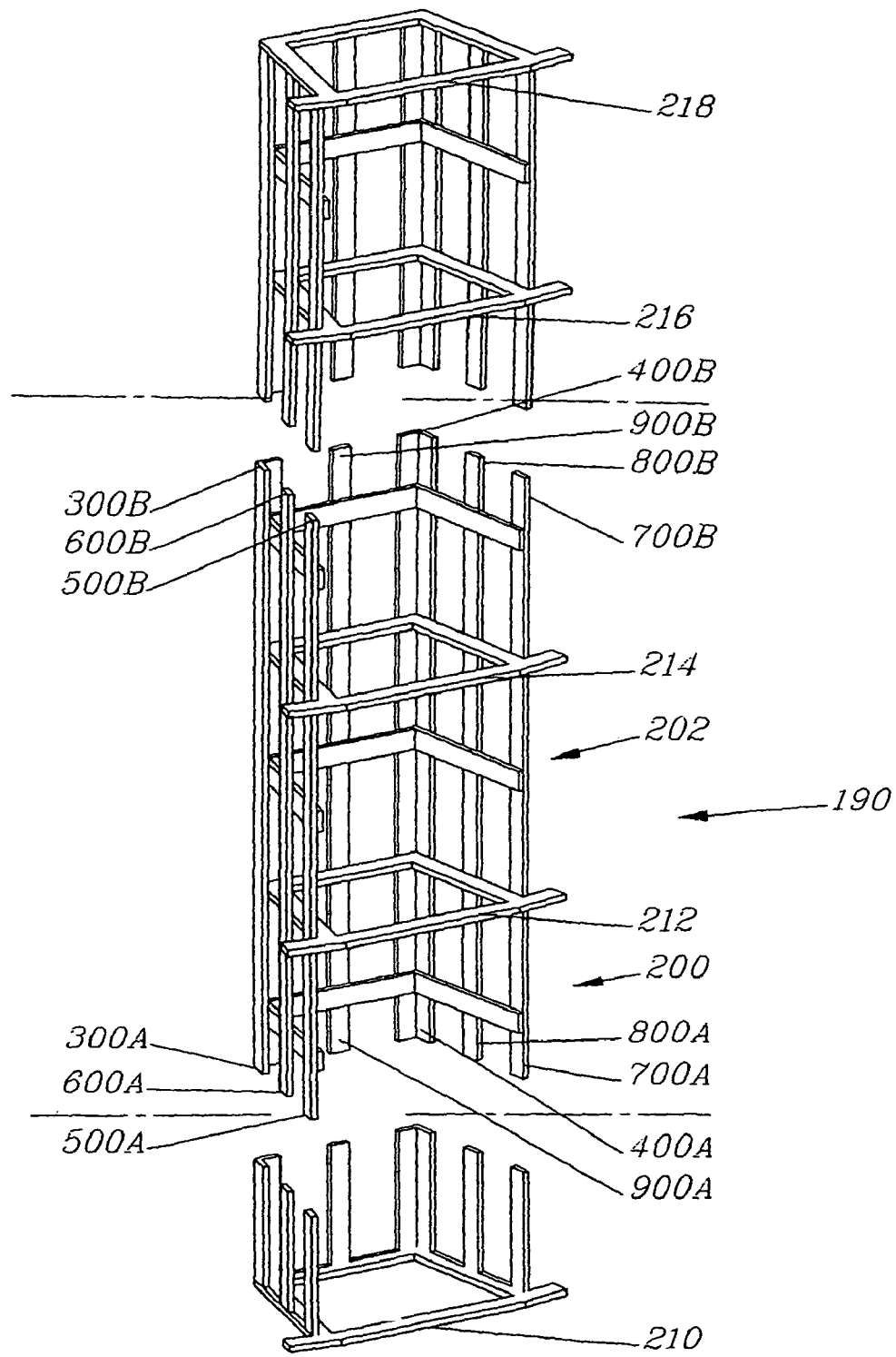
FIG. 7 is an exploded view of the invention of FIG. 4 where span (190) has been severed along a first cross-section and a second cross-section to create an implant with supports or spikes (300, 400, 500, 600, 700, 800 and 900) at first end of the implant and supports or spikes (304, 404, 504, 604, 704, 804 and 904) exposed at the opposite and second end of span (190).

FIG. 7 is an exploded view of the invention of FIG. 6 where span (190) has been severed along a first cross-section and a second cross-section to create an implant with supports or spikes (300A, 400A, 500A, 600A, 700A, 800A and 900A) at first end of the implant and supports or spikes (300B, 400B, 500B, 600B, 700B, 800B and 900B) exposed at the opposite and second end of span (190).

Figure 8:
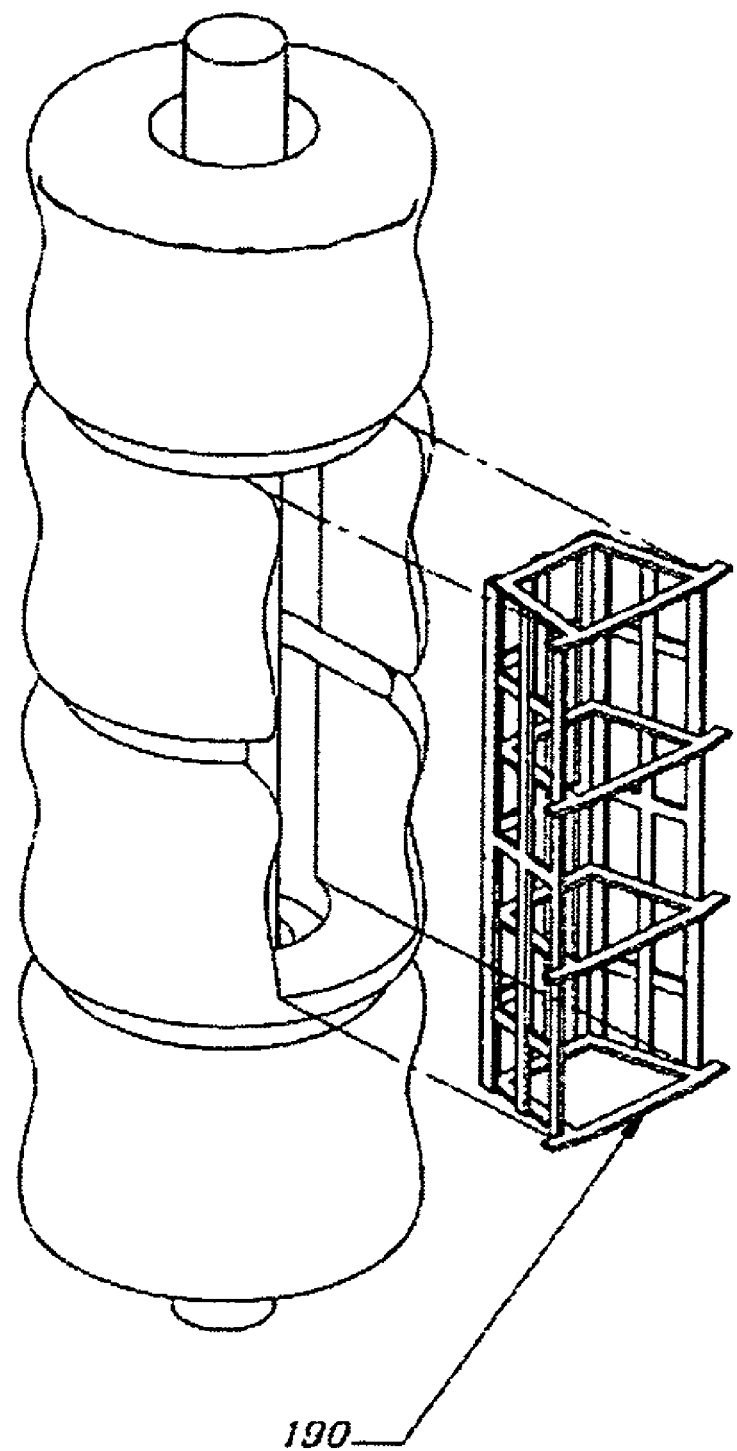
FIG. 8 is a perspective of a surgically created cavity in a vertebra and an embodiment of the present invention.
Figure 11:
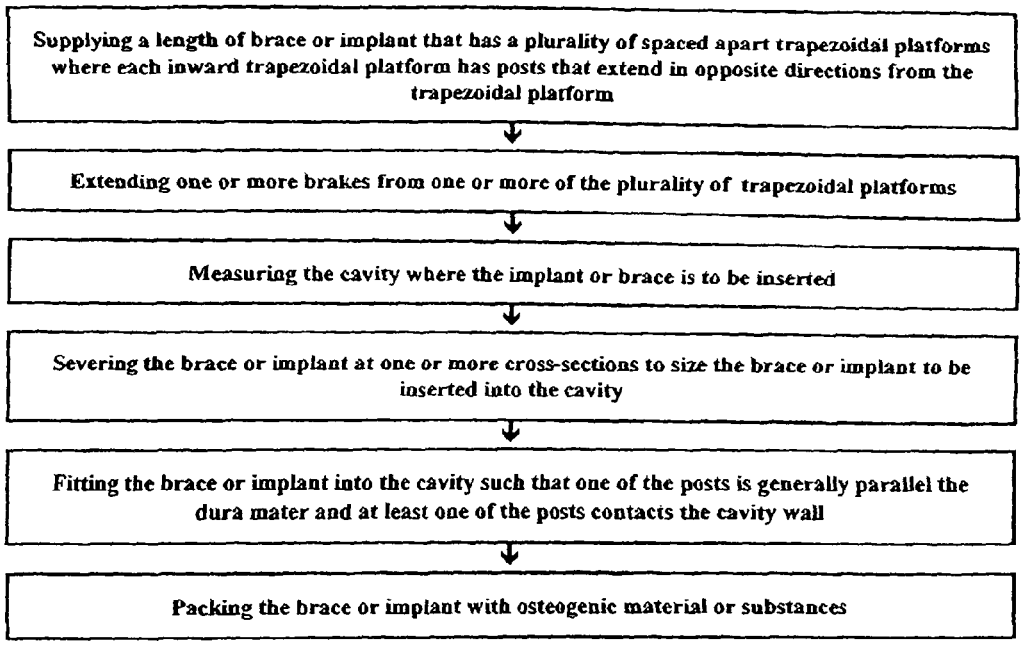
FIG. 11 is another diagrammatic representation of the steps of still another embodiment of the present invention.
Figure 12:
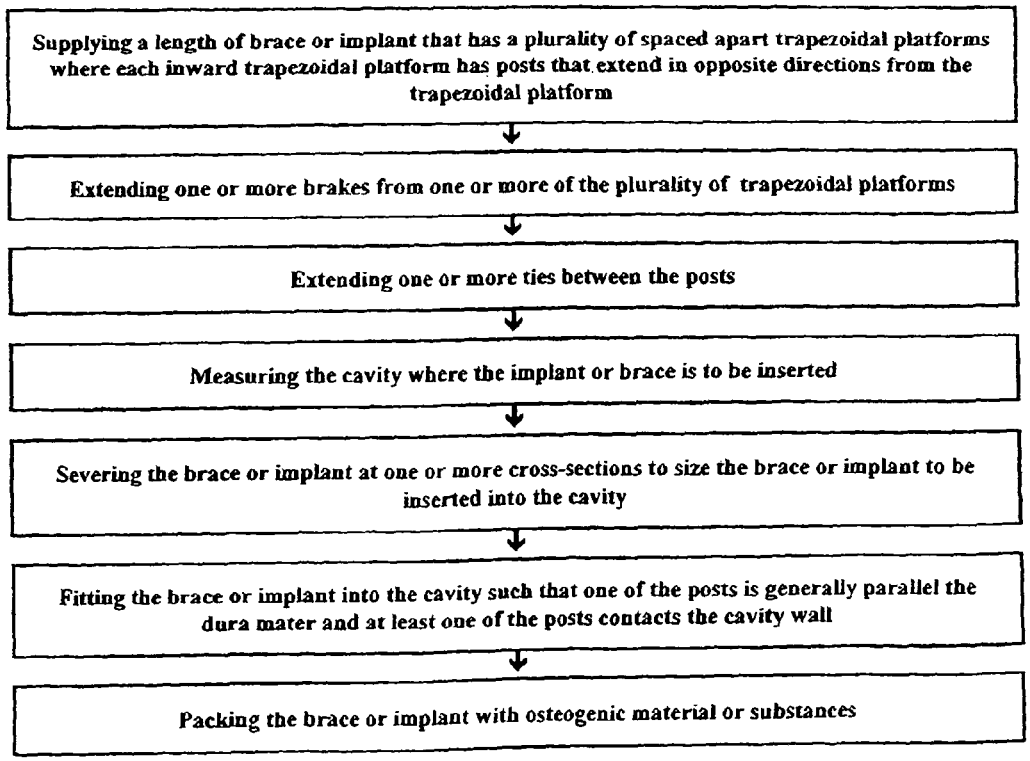
FIG. 12 is yet another exemplification of the steps of yet another embodiment of the present invention.

FIG. 8 portrays an embodiment of a span (190) of the present invention that can be inserted into a surgically created cavity of a vertebra.

Steps associated with the practice of the methods of embodiments the present invention are set forth in FIGS. 9-12. Those steps are related to the practice of using the spinal implant structures previously set forth. Moreover, the majority of the preferred embodiments of the present invention practice the packing of osteogenic materials or substances into the implant's receptacle after the brace has been inserted into the cavity. Importantly, preferred methods of the current invention can be used to create implants that have a trapezoidal platform at each end of the implant, a trapezoidal platform at the first end of the brace and a set of spikes corresponding to the posts at the second end of the implant or a set of spikes at each end of the implant.

Figure 13:
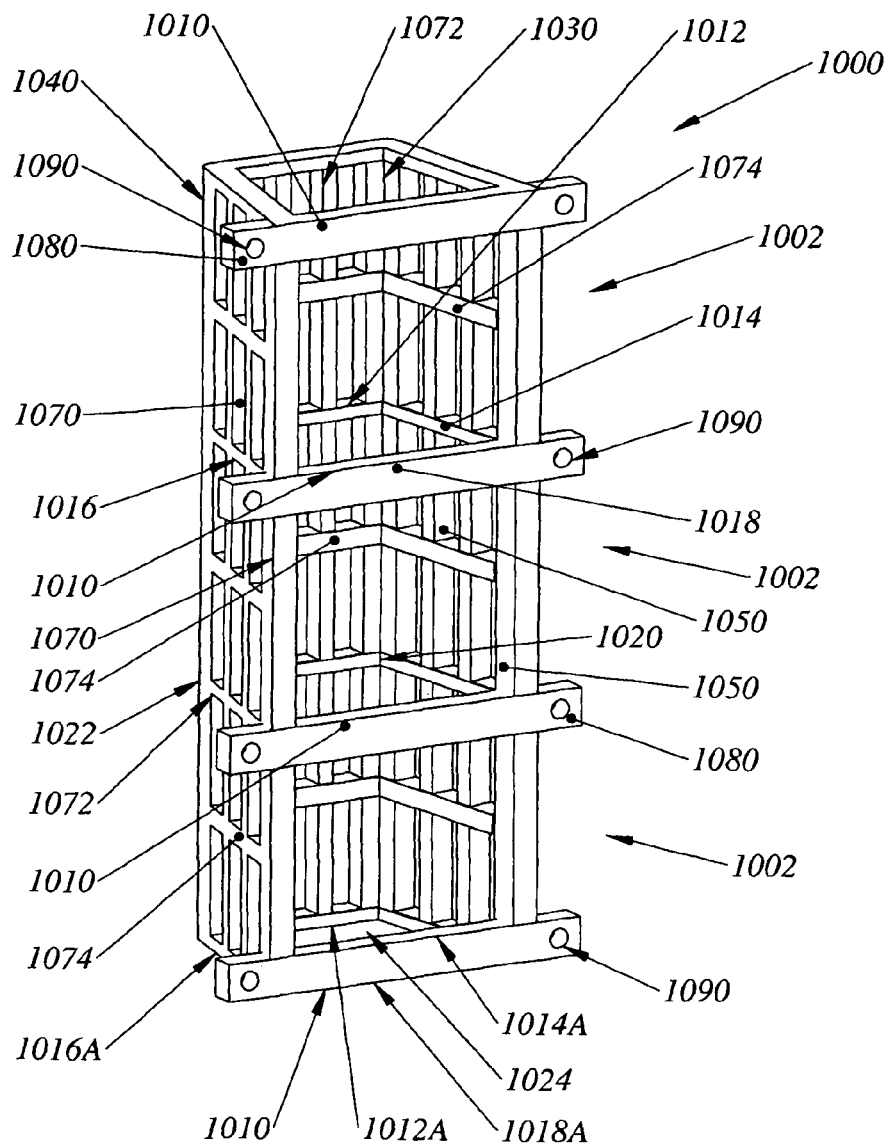
FIG. 13 is a frontal perspective of an embodiment of implant of the present invention.

FIG. 13 portrays a span (1000) of receptacles (1002) that can be packed with osteogenic materials prior to the completion of spinal surgery. Span (1000) is manufactured of titanium, stainless steel, resorbable polymers, non-resorbable polymers or combinations thereof. By way of illustration, generally horizontal divider (1010) has inward side (1012) (after insertion into the surgically created cavity, positioned near the dura mater of the spinal cord), long outward side (1018), first converging side (1014) and second converging side (1016). As shown, span (1000) includes a plurality of dividers (1010), including intermediate or interior, superior and inferior dividers (1010). Superior divider (1010) can function as a top of span (1000) while inferior divider (1010) can function as a base of implant (1000). Intersection of first converging side (1014) and short side (1012) creates first corner (1020) and intersection of inward side (1012) and second converging side (1016) creates second corner (1022), such that each divider (1010) has first corner (1020) and second corner (1022). In select embodiments, inward edges (1012A, 1014A, 1016A and 1018A) of inward side (1012), long side (1018), first converging side (1014) and second converging side (1016) create generally trapezoidal aperture (1024), while in other embodiments, inward edges are constructed to create an aperture of other than trapezoidal dimensions. First universal corner post (1030) contacts first corners (1020) and second universal corner post (1040) contacts second corners (1022). In the embodiment disclosed in FIG. 13, first universal corner post (1030) is angled at about ninety degrees to simultaneously connect with inward side (1012) and first converging side (1014) and second universal corner post (1040) is angled at about ninety degrees to simultaneously connect with inward side (1012) and second converging side (1016).

In select embodiments, one or more first side universal posts (1050) can contact first converging sides of dividers (1010) of span (1000) while one or more second side universal posts (1070) can contact second converging sides of dividers (1010) of span (1000). One of the first side universal posts (1050) can function as a third corner post and one of the second side universal posts (1070) can function as a fourth corner post. In other embodiments, one or more inward universal posts (1072) can contact short sides of dividers (1010). Implant (1000) can also include one or more ties (1074) contacting universal corner posts (1030, 1040) and universal posts (1050, 1070, 1072). Most preferably, ties (1074) are positioned on the inward sides of the universal posts.

As shown in FIG. 13, the combination of the interior generally horizontal dividers, the inferior generally horizontal divider, the superior generally horizontal divider, the universal corner posts (1030, 1040) and the universal posts (1050, 1070, 1072) contacting the first and second converging sides of span (1000) creates openings of more than one cross-sectional area about the outer border of the span or implant (1000)—allowing the surgeon to see through the openings, prior to the addition of osteogenic substances into implant (1000).

In the FIG. 13 embodiment, implant (1000) is provided with a plurality of brakes (1080) integral with one or more long outward sides (1018) of generally horizontal dividers (1010). However, in other embodiments of current invention, brakes (1080) need not be integral with outward sides (1018) of generally horizontal dividers (1010), and brakes (1080) can be affixed with outward universal posts (1050, 1070). One or more brakes (1080) are provided with bore (1090). Brakes (1080) extend laterally beyond first converging sides and second converging sides of dividers (1010) of implant (1000). Brakes (1080) assist the surgeon in minimizing potential damage to the spinal cord from over-insertion of the implant into the surgically created cavity.

Figure 14:
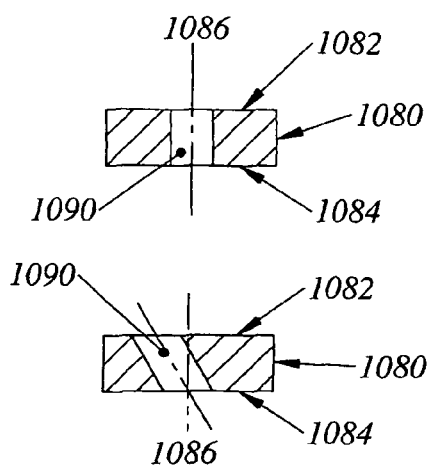
FIG. 14 is a cross section of an embodiment of a brake of the present invention.

Depending on predetermined engineering parameters, as shown in FIG. 14, brake (1080) can include bore (1090) that is perpendicular to outward side (1082) and inward side (1084) of brake (1090) or brake (1080) can include bore (1090) that is angled at other than perpendicular from the outward side (1082) and inward side (1084) of brake (1080). It has been discovered that bore (1090) can be angled from about 1 degree to about 60 degrees away from the bore's reference axis (1086), where the reference axis (1086) equates to the perpendicular axis between outward side (1082) and inward side (1084) of brake (1080).

In select preferred embodiments, bores (1090) of brakes (1080) associated with superior generally horizontal divider (1010) as well as the bores (1090) of brakes (1080) associated with generally horizontal dividers (1010) in proximity with superior divider (1010) are angled upward from outward side (1082) through inward side (1084) of brake (1080) and bores (1090) of brakes (1080) associated with inferior generally horizontal divider (1010) as well as the bores (1090) of brakes (1080) associated with generally horizontal dividers (1010) in proximity with inferior divider (1010) are angled downward from outward side (1082) through inward side (1084) of brake (1080). Bores (1090) function to receive a fastener, such as a screw (not shown in this view) that assists in securing the implant to bone.

Turning to the embodiment disclosed in FIG. 15, implant (1000) is provided with a superior plate (1100) attached to outward side (1018) of an upper or superior divider (1010). In similar fashion, inferior plate (1200) is attached to outward side (1018) of a lower or inferior divider (1010). Upper plate (1100) has two bores (1102) for receiving fasteners to assist in securing implant (1000) to bone. Lower plate (1200) includes two bores (1202) for receiving fasteners that assist in securing span (1000) to bone. Although upper plate (1100) and lower plate (1200) are shown with a plurality of bores, Applicant's current invention can function when upper plate (1100) and lower plate (1200), each include only a single bore (1102, 1202).

As shown in the embodiment of FIG. 15, superior plate (1100) extends upward from superior divider (1010) and inferior plate (1200) depends downward from inferior divider (1010). In select embodiments, superior plate (1100) extends upward in a plane perpendicular to outward side (1018) of upper divider (1010) and inferior plate (1200) depends downward in a plane perpendicular to outward side (1018) of lower divider (1010). Intermediate dividers (1010) include one or more brakes (1080) having bore (1090). Brakes (1080) extend laterally beyond first converging sides and second converging sides of dividers (1010) of implant (1000).

With reference to FIG. 16, plate (1100) can include one or more bores (1102) where each bore (1102) is perpendicular to outward side (1104) and inward side (1106) of plate (1100) or plate (1100) can include one or more bores (1102) that are angled at other than perpendicular from the outward side (1104) and inward side (1106) of plate (1100). By way of example, bores (1102) can be angled from about 1 degree to about 60 degrees away from the bore's reference axis (1110), where the reference axis (1110) equates to the perpendicular axis between outward side (1104) and inward side (1106) of plate (1000). Plate (1200) and one or more bores (1202) are manufactured in a similar fashion to plate (1100) and one or more bores (1102).

In select preferred embodiments, bores (1102) of plate (1100) are angled upward from outward side (1104) through inward side (1106) of plate (1100) and bores (1202) of plate (1200) are angled downward from the outward side of plate (1200) through the inward side of plate (1200) One or more bores (1102, 1202) function to receive a fastener, such as a screw (not shown in this view) that assists in securing the implant to bone. Brakes (1080) and bores (1090) of the FIG. 15 embodiment are identical to brakes (1080) and bores (1090) of the FIG. 13 embodiment. Bores (1090) of brakes (1080) in proximity with superior plate (1100) can be angled upward while bores (1090) of brakes in proximity with inferior plate (1200) can be angled downward.

With reference to an embodiment portrayed in FIG. 17, implant (1000) is provided with superior divider (1010) that includes a plurality of bores (1092) integral with outward side (1018) and inward edge (1018A) of superior divider (1010) and inferior divider (1010) includes a plurality of bores (1092) integral with outward side (1018) and inward edge (1018A) of inferior divider (1010). Bores (1092) are inset from first converging sides (1014) and second converging sides (1016) of dividers (1010) of implant (1000). As depicted in FIG. 18, superior divider (1010) includes one or more bores (1092) where each bore (1092) is angled at other than perpendicular from the outward side (1018) and inward edge (1018) of divider (1010). Bores (1092) can be angled from about 1 degree to about 60 degrees away from the bore's reference axis (1096), where the reference axis (1096) equates to the perpendicular axis between outward side (1018) and inward edge (1018A) of divider (1010). Inferior divider (1010) and one or more bores (1092) are manufactured in a similar fashion to superior (1010) and one or more bores (1010).

In the preferred embodiments, bores (1092) of superior divider (1010) are angled upward from outward side (1018) through inward edge (1018A) of superior divider (1010) and bores (1092) of inferior divider (1010) are angled downward from the outward side (1018) through inward edge (1018A) of inferior divider (1010). Bores (1092) function to receive a fastener, such as a screw (not shown in this view) that assists in securing the implant to bone. Brakes (1080) and bores (1090) of the FIG. 17 embodiment are identical to brakes (1080) and bores (1090) of the FIG. 13 embodiment. Bores (1090) of brakes (1080) in proximity with superior divider (1010) can be angled upward while bores (1090) of brakes (1080) in proximity with inferior divider (1010) can be angled downward.

Figure 19:
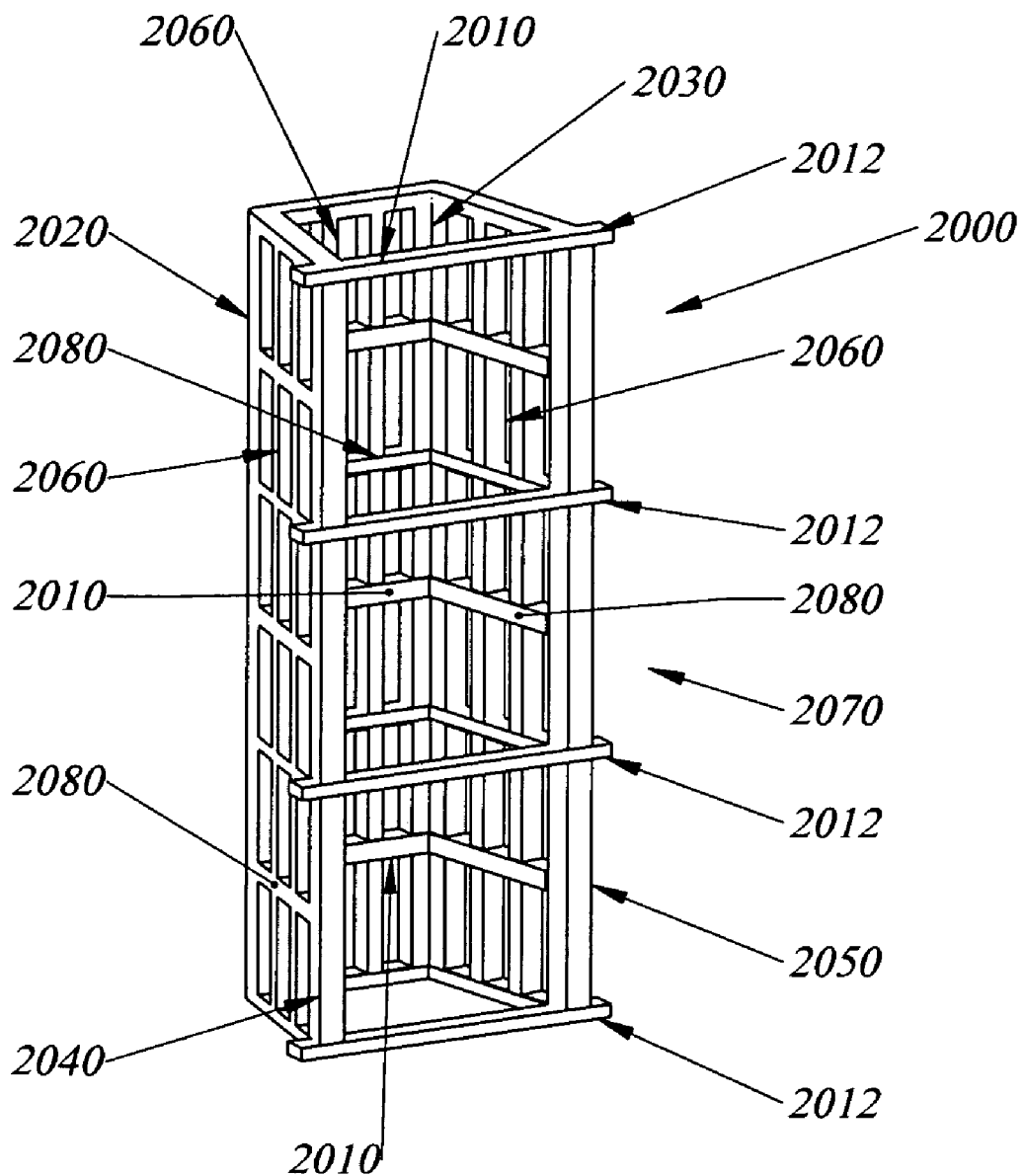
FIG. 19 is a perspective of an embodiment of implant and its face of the present invention.

FIG. 19 enables an implant (2000) that can be inserted into a surgically created cavity. Implant (2000) is provided with a series of dividers (2010), first corner post (2020), second corner post (2030), third corner post or first outward vertical post (2040) and fourth corner post or second vertical outward post (2050). The vertical length of implant (2000) and the number of dividers (2010) are manufacture in accordance with predetermined engineering parameters. In select embodiments, implant (2000) can also include posts (2060) and ties (2080).

Dividers (2010) have cross members or outward edges (2012) that contact third generally vertical corner post (2040) and fourth generally vertical corner post (2050). The combination of cross members (2012), third corner post (2040) and fourth corner post (2050) create face (2070) of implant (2000). After insertion into the surgically created cavity, face (2070) of implant (2000) is proximate the surgeon. Although not shown FIG. 19, select embodiments of implant (2000) can include brakes and/or plates similar to those disclosed in FIGS. 13, 14, 15, 16 17 and 18.

Figure 20:
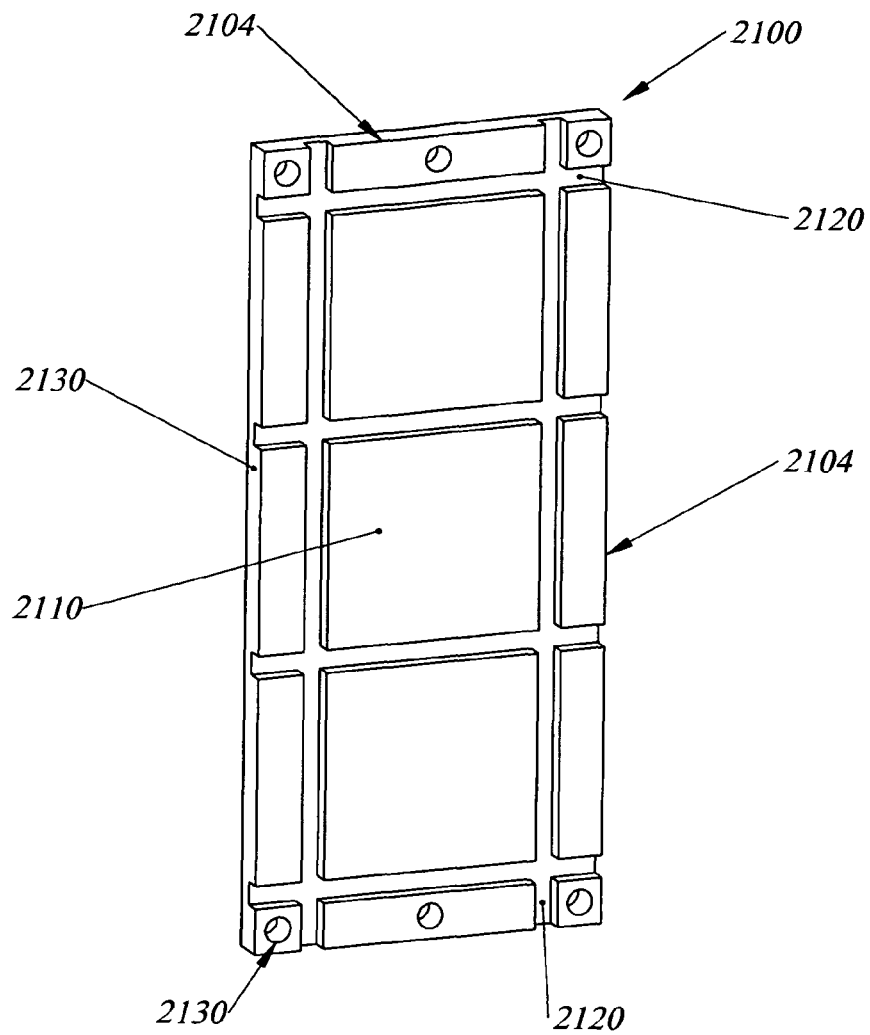
FIG. 20 is a perspective of an overlay within the scope of the present invention.

FIG. 20 is a perspective of an embodiment of an overlay (2100) within the scope of the present invention. As shown in FIG. 20, inward surface (2110) of overlay (2100) has indentations, channels or grooves (2120) and apertures (2130) proximate one or more margins (2104) of overlay (2100). Sidewalls (2130) extended between inward surface (2110) and outward generally smooth surface (not shown in this view). Indentured inward surface (2110) is manufactured to interlock with face (2070) of implant (2000). In the FIG. 20 embodiment, overlay (2100) is quadrilateral, but when engineering parameters require, other embodiments of overlays (2100) can include dimensions other than quadrilateral, e.g., polygonal.

Figure 21:
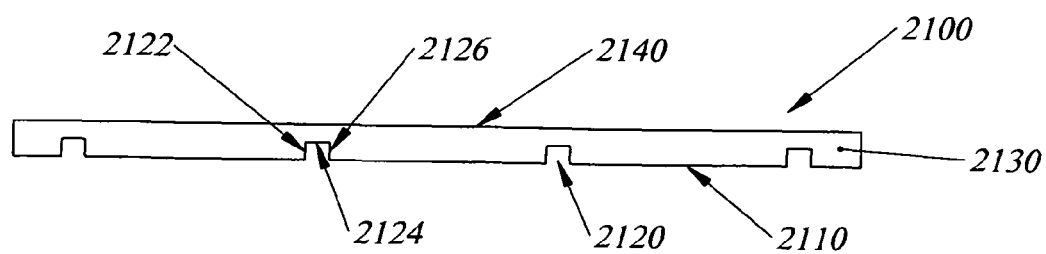
FIG. 21 is a side view of an overlay within the scope of the present invention.

FIG. 21 is a side view of an embodiment of overlay (2100) within the scope of the present invention. Outward surface (2140) is generally smooth and inward surface (2110) is indentured. Sidewall (2130) extends between generally smooth outward surface (2140) and inward surface (2110). As shown in FIG. 21, each channel or groove (2120) has three sides (2122, 2124, 2126) that intersect at right angles. However, other embodiments of overlay (2100) can include channels or grooves (2120) that do not have three sides intersecting at right angles.

Figure 22:
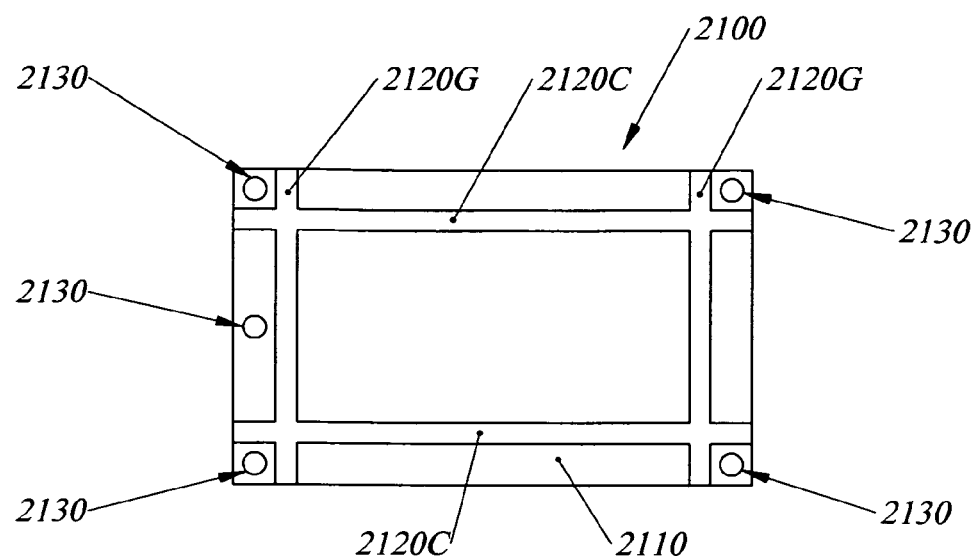
FIG. 22 is a plan view of an inward side of an embodiment of an overlay within the ambit of the present invention.

FIG. 22 is a plan view of inward surface (2110) of an embodiment of overlay (2100). When using the FIG. 22 embodiment, the surgeon inserts fasteners, such as screws, through apertures (2130) into bone, where apertures (2130) are situated traverse to both the implant and the surgically created cavity into which the implant is inserted before the implant is covered with overlay (2100). Inward surface (2110) is provided with first generally vertical groove (2120G), second vertical groove (2120G) and a plurality of generally transverse channels (2120C) connected with first generally vertical groove (2120G) and second vertical groove (2120G). First generally vertical groove (2120G), second generally vertical groove (2120G) and generally transverse channels (2120C) are designed to interlock with all or part of face (2070) of implant (2000).

Figure 23:
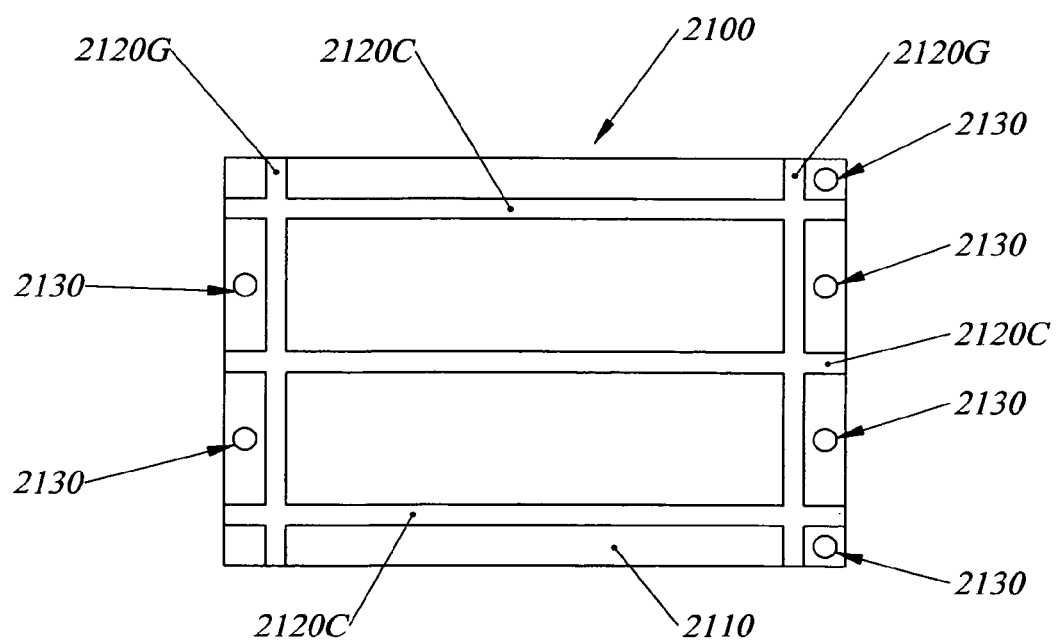
FIG. 23 is a plan view of an inward side of another embodiment of an overlay within the ambit of the present invention.

FIG. 23 is a plan view of inward surface (2110) of another embodiment of overlay (2100). When using the FIG. 23 embodiment, the surgeon inserts fasteners, such as screws, through apertures (2130) into bone, where the apertures (2130) are situated traverse to both the implant and the surgically created cavity into which the implant is inserted before the implant is covered with overlay (2100). Inward surface (2110) is provided with first generally vertical groove (2120G), second generally vertical groove (2120G) and a plurality of generally transverse channels (2120C) connected with first generally vertical groove (2120G) and second vertical groove (2120G). First generally vertical groove (2120G), second generally vertical groove (2120G) and generally transverse channels (2120C) are designed to interlock with all or part of face (2070) of implant (2000).

Figure 24:
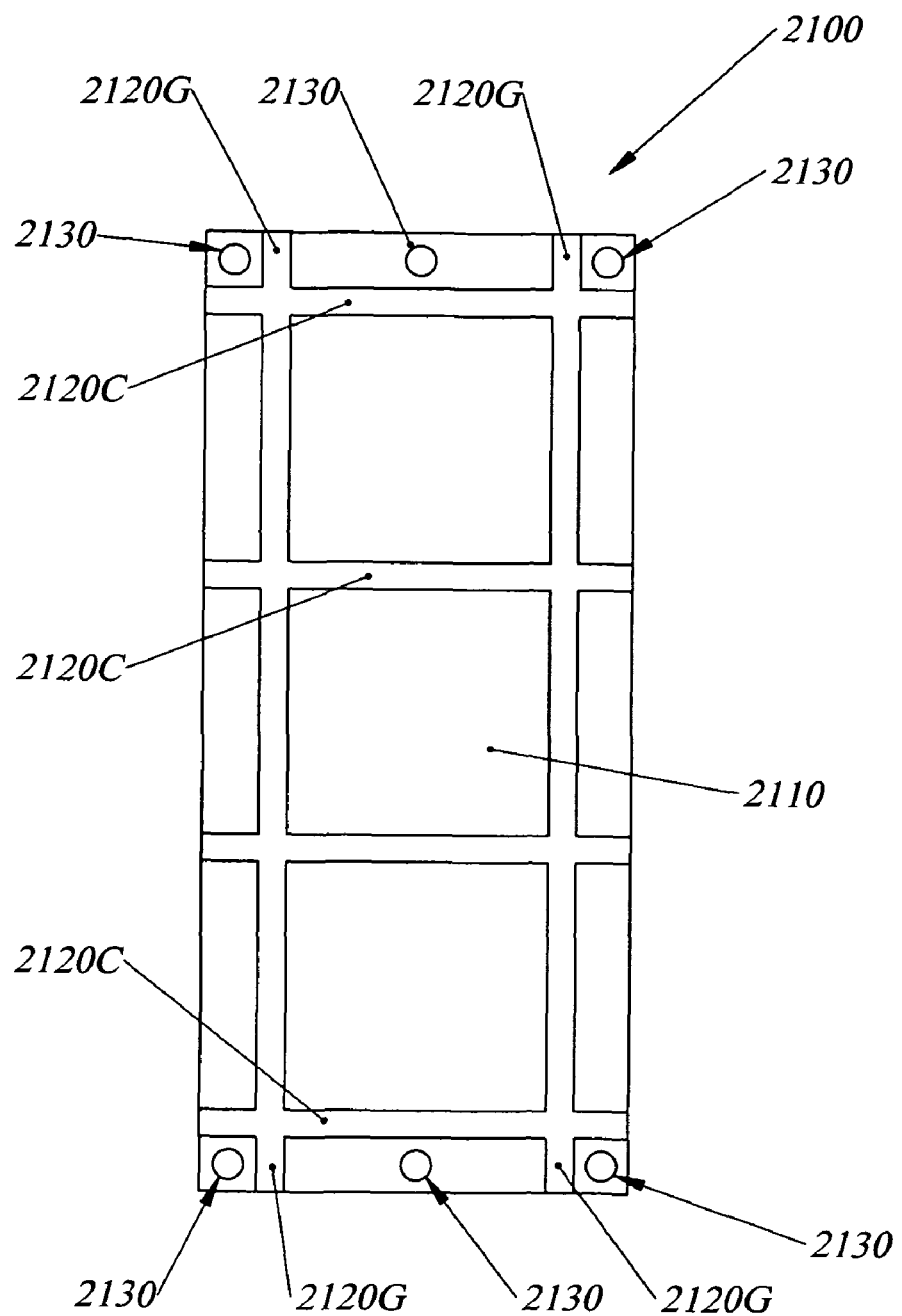
FIG. 24 is a plan view of an inward side of yet another embodiment of an overlay within the ambit of the present invention.

FIG. 24 is a plan view of inward surface (2110) of still another embodiment of overlay (2100). When using the FIG. 24 embodiment, the surgeon inserts fasteners, such as screws, through apertures (2130), where apertures (2130) are above and below the implant and the surgically created cavity into which the implant is inserted before the implant is covered with overlay (2100). Inward surface (2110) is provided with first generally vertical groove (2120G), second generally vertical groove (2120G) and a plurality of generally transverse channels (2120C) connected with first generally vertical groove (2120G) and second vertical groove (2120G). First generally vertical groove (2120G), second generally vertical groove (2120G) and generally transverse channels (2120C) are designed to interlock with all of face (2070) of implant (2000).

Steps associated with the practice of the methods of embodiments the present invention are set forth in FIGS. 25-29. Those steps are related to the practice of using the spinal implant structures previously set forth.

Having disclosed the invention as required by Title 35 of the United States Code, Applicant now prays respectfully that Letters Patent be granted for his invention in accordance with the scope of the claims appended hereto.

What is claimed is:

1. In combination, an implant capable of implantation into a surgically created cavity between a superior vertebra and an inferior vertebra and an overlay capable of covering said implant:
   I) said implant, comprising:
   a) a series of dividers;
   b) a first corner post contacting first inward corners of said series;
   c) a second corner post contacting second inward corners of said series;
   d) a third corner post contacting first outward corners of said series; and
   e) a fourth corner post contacting second outward corners of said series; and
   II) said overlay, capable of covering said implant, comprising:
   a) an outward generally smooth surface;
   b) an inward surface opposite said outward generally smooth surface, wherein said inward surface comprises indentations for interlocking with outward edges of said series, said third corner post and said fourth corner post;
   c) sidewalls extending between said outward generally smooth surface and said inward surface; and
   d) one or more apertures extending through said overlay, wherein said one or more apertures are proximate to one or more margins of said overlay.

2. The invention of claim 1, wherein said implant further comprises:
   a) one or more posts contacting said series and positioned between said first corner post said third corner post; and
   b) one or more posts contacting said series and positioned between said second corner and said fourth corner, wherein prior to addition of osteogenic substances into said implant, a surgeon can see through said openings created by said posts and said dividers.

3. The invention of claim 2 further comprising:
   a) one or more first side brakes attached to said third corner post and extending laterally beyond first sides of said series; and
   b) one or more second side brakes attached to said fourth corner posts and extending laterally beyond second sides of said series.

4. The invention of claim 3, wherein one or more of said first side brakes and one or more of said second side brakes comprises a bore.

5. The invention of claim 3 further comprising:
   a) a first plate, comprising a plurality of bores, attached to a superior divider of said series; and
   b) a second plate, comprising a plurality of bores, attached to an inferior divider of said series.

6. The invention of claim 5, wherein said first plate extends above said superior divider and said second plate depends downward from said inferior divider of said series.

7. The invention of claim 2, wherein said overlay is quadrilateral.

8. The invention of claim 7, wherein said indentations comprise:
   a) a first groove proximate a first side of said overlay;
   b) a second groove proximate a second side of said overlay; and
   c) a plurality of generally transverse channels interconnected with said first groove and said second groove.

* * * * *